United States Patent
Rasmussen et al.

(10) Patent No.: US 7,214,368 B2
(45) Date of Patent: *May 8, 2007

(54) THERAPEUTIC REGIMEN FOR TREATING CANCER COMPRISING THE ADMINISTRATION OF ADENOVIRAL VECTORS COMPRISING A TNF-α TRANSGENE

(75) Inventors: Henrik S. Rasmussen, Arnold, MD (US); Karen W. Chu, New York, NY (US)

(73) Assignee: GenVec, Inc., Gaithersburg, MD (US)

( * ) Notice: Subject to any disclaimer, the term of this patent is extended or adjusted under 35 U.S.C. 154(b) by 589 days.

This patent is subject to a terminal disclaimer.

(21) Appl. No.: 10/151,633

(22) Filed: May 17, 2002

(65) Prior Publication Data

US 2003/0086904 A1    May 8, 2003

Related U.S. Application Data

(63) Continuation-in-part of application No. 10/001,017, filed on Nov. 2, 2001.

(51) Int. Cl.
*A01N 63/00* (2006.01)
*A01N 65/00* (2006.01)
*A01N 43/04* (2006.01)
*A61K 31/70* (2006.01)
*C12N 15/00* (2006.01)

(52) U.S. Cl. ............ 424/93.1; 514/44; 435/320.1; 536/23.1; 536/23.52; 536/24.1; 800/21

(58) Field of Classification Search ............... 514/44; 424/93.1; 800/21
See application file for complete search history.

(56) References Cited

U.S. PATENT DOCUMENTS

| | | | |
|---|---|---|---|
| 4,879,226 A | 11/1989 | Wallace et al. | 435/68.1 |
| 5,206,152 A | 4/1993 | Sukhatme | 435/69.1 |
| 5,288,852 A | 2/1994 | Yamada et al. | 530/351 |
| 5,324,655 A | 6/1994 | Kriegler et al. | 435/357 |
| 5,422,104 A | 6/1995 | Fiers et al. | 424/85.1 |
| 5,571,797 A | 11/1996 | Ohno et al. | 514/44 |
| 5,612,318 A | 3/1997 | Weichselbaum et al. | 514/44 |
| 5,624,830 A | 4/1997 | Mullen et al. | 435/456 |
| 5,641,755 A | 6/1997 | Weichselbaum et al. | 514/44 |
| 5,652,353 A | 7/1997 | Fiers et al. | 536/23.5 |
| 5,677,178 A | 10/1997 | McCormick | 435/325 |
| 5,763,209 A | 6/1998 | Sukhatme | 435/69.1 |
| 5,770,581 A | 6/1998 | Weichselbaum et al. | 514/44 |
| 5,801,029 A | 9/1998 | McCormick | 424/93.2 |
| 5,817,636 A | 10/1998 | Weichselbaum et al. | 514/44 |
| 5,846,945 A | 12/1998 | McCormick | 514/44 |
| 5,851,806 A | 12/1998 | Kovesdi et al. | 435/91.41 |
| 5,856,181 A | 1/1999 | McCormick | 435/325 |
| 5,863,797 A | 1/1999 | Kriegler et al. | 435/366 |
| 5,962,424 A | 10/1999 | Hallahan et al. | 514/44 |
| 5,968,735 A | 10/1999 | Stein et al. | 435/6 |
| 5,972,706 A | 10/1999 | McCormick | 435/440 |
| 5,993,800 A | 11/1999 | Linsley et al. | 424/93.21 |
| 6,066,624 A | 5/2000 | Woo et al. | 514/44 |
| 6,254,862 B1 | 7/2001 | Little et al. | 424/93.1 |
| 6,271,207 B1 | 8/2001 | Cristiano et al. | 514/44 |
| 6,281,010 B1 | 8/2001 | Gao et al. | 435/325 |
| 6,297,219 B1 | 10/2001 | Nabel et al. | 514/44 |
| 6,337,338 B1 | 1/2002 | Kozlowski et al. | 514/311 |

FOREIGN PATENT DOCUMENTS

| | | |
|---|---|---|
| DE | 197 47 718 A | 5/1999 |
| EP | 0 155 549 A | 9/1985 |
| EP | 0 869 180 A | 10/1998 |
| WO | WO 92/11033 A | 7/1992 |
| WO | WO 93/19191 A | 9/1993 |
| WO | WO 94/06916 A | 3/1994 |
| WO | WO 94/21792 A | 9/1994 |
| WO | WO 95/06120 A | 3/1995 |
| WO | WO 95/34671 A | 12/1995 |
| WO | WO 96/27021 A | 9/1996 |
| WO | WO 96/33746 A | 10/1996 |
| WO | WO 97/12623 A | 4/1997 |
| WO | WO 97/20051 A | 6/1997 |
| WO | WO 98/00166 A | 1/1998 |
| WO | WO 98/46779 A | 10/1998 |
| WO | WO 98/46781 A | 10/1998 |
| WO | WO 98/55622 A | 12/1998 |
| WO | WO 99/00518 A | 1/1999 |
| WO | WO 99/16889 A | 4/1999 |
| WO | WO 99/21589 A | 5/1999 |
| WO | WO 99/23216 A | 5/1999 |
| WO | WO 99/46371 A | 9/1999 |
| WO | WO 99/47690 A | 9/1999 |
| WO | WO 99/55831 A | 11/1999 |
| WO | WO 99/65515 A | 12/1999 |
| WO | WO 00/14255 A | 3/2000 |
| WO | WO 00/23088 A | 4/2000 |
| WO | WO 00/39319 A | 7/2000 |

(Continued)

OTHER PUBLICATIONS

Deonarain (1998) Exp. Opin. Ther. Pat., 8(1): 53-69.*

(Continued)

*Primary Examiner*—Joseph Woitach
*Assistant Examiner*—Robert M. Kelly
(74) *Attorney, Agent, or Firm*—Leydig, Voit & Mayer, Ltd.

(57) ABSTRACT

The invention provides a method for treating a tumor in a human comprising administering to the tumor a dose of a pharmaceutical composition comprising (i) a pharmaceutically acceptable carrier and (ii) an adenoviral vector comprising a nucleic acid sequence encoding TNF-α operably linked to a promoter, wherein the dose comprises about $1 \times 10^7$ to about $4 \times 10^{12}$ particle units (pu) of replication-deficient adenoviral vector, at least once in a therapeutic period comprising up to 10 weeks, whereby the tumor in human is treated.

16 Claims, 3 Drawing Sheets

FOREIGN PATENT DOCUMENTS

| | | |
|---|---|---|
| WO | WO 00/44922 A | 8/2000 |
| WO | WO 01/24684 A | 4/2001 |
| WO | WO 02/00906 A | 1/2002 |
| WO | WO 02/080849 A | 10/2002 |

OTHER PUBLICATIONS

Gorecki (2001) Exp. Opin. Emerging Drugs, 6(2): 187-98.*
Verma, et al. (1997) Nature, 389: 239-42.*
Eck, et al. (1996) Goodman & Gilman's The Pharmacological Basis of Therapeutics, 9th Ed., McGraw-Hill, New York, NY., pp. 77-101.*
Luo, et al. (2004) Trends in Biotechnology, 22(3): 101-03.*
Somia, et al. (2000) Nature Reviews: Genetics, "Gene Therapy: Trials and Tribulations", 1: 91-99.*
Hallahan et al., Am. J. Clin. Oncol., 24 (5), 473-480 (2001).
Kurihara et al., J. Clin. Invest., 106(6), 763-771 (Sep. 2000).
Weichselbaum et al., Lancet Oncol., 3, 665-671 (Nov. 2002).
Baher et al., Anticancer Research, 19 (4B), 2917-2924 (Jul.-Aug. 1999).
Blankenstein et al., J. Exp. Med., 173, 1047-1052 (1991).
Block et al., Arch. Surg., 127, 1330-1334 (1992).
Brough et al., J. Virol., 70 (9), 6497-6501 (1996).
Chung et al., Cancer Gene Ther., 5 (6), 344-349 (1998).
Creaven et al., Cancer Chemother. Pharmacol., 20, 137-144 (1987).
Eggermont et al., Ann. Surg., 224 (6), 756-765 (1996).
Fiers et al., Proc. Am. Assoc. Cancer Res., 34, 581-582 (1993).
Fujii et al., Blood, 93 (12), 4328-4335 (1999).
Ginsberg et al., Bull. New York Acad. Med., 73 (1), 53-58 (1996).
Gridley et al., Anticancer Res., 14, 1107-1112 (1994).
Gridley et al., Anticancer Res., 20 (6B), 4195-4203 (Nov.-Dec. 2000).
Gridley et al., Oncol. Res., 9, 217-227 (1997).
Hallahan et al., Nat. Med., 1 (8), 786-791 (1995).
Hallahan et al., Proceedings of ASCO, 15, p. 84, Abstract 3, (1996).
Haranaka et al., Int. J. Cancer, 34, 263-267 (1984).
Hersh et al., Gene Ther., 2, 124-131 (1995).
Hu et al., Cancer Res., 57, 3339-3343 (1997).
Isobe et al., Biochem. Biomed. Res. Comm., 202 (3), 1538-1542 (1994).
Jones et al., Cancer Surveys, 8 (4), 817-836 (1989).
Jones et al., Progress in Growth Factor Res., 1, 107-122 (1989).
Koshita et al., Int. J. Cancer, 63, 130-135 (1995).
Lejeune, Eur. J. Cancer, 31A (6), 1109-1016 (1995).
Leonard et al., J. Urol., 148, 743-746 (1992).
Manusama et al., Seminars in Surgical Oncology, 14, 232-237 (1998).
Marr et al., Cancer Gene Ther., 6 (5), 465-474 (1998).
Marr et al., Gene Ther., 4, 1181-1188 (1997).
Marr et al., Int. J. Onconology, 12, 509-515 (1998).
Martinet et al., Am. J. Respir. Cell Mol. Biol., 6, 510-515 (1992).
Mauceri et al., C. R. Acad. Sci. Series III, 322 (2-3), 225-228 (Feb. 1999).
Mauceri et al., Cancer Res., 56, 4311-4314 (1996).
Mauceri et al., Proc. Am. Assoc. Cancer Res., 37, p. 347, Abstract 2365, (1996).
Mauceri et al., Radiation Oncology Investigations, 5, 220-226 (1997).
Morsy et al., PNAS USA, 95, 7866-7871 (Jul. 1998).
Mulé, Proc. Am. Assoc. Cancer Res., 34, 581 (1993).
Porter, Trends in Biotechnology, 9, 158-162 (1991).
Richards et al., Ann. New York Acad. Sci., 762, 282-293 (1995).
Sata et al., Cancer Res., 58, 1677-1683 (1998).
Sersa et al., Int. J. Cancer, 42, 129-134 (1988).
Seung et al., Cancer Res., 55, 5561-5565 (1995).
Slesarev et al., Medical Oncology, 15, 37-43 (1998).
Sparmann et al., Int. J. Cancer, 59, 103-107 (1994).
Spriggs et al., in: Tumor Necrosis Factors: The Molecules and Their Emerging Role in Medicine, Chapter 25, 383-406 (Raven Press, Ltd., New York, NY, 1992).
Spriggs et al., J. Nat. Cancer Inst., 80 (13), 1039-1044 (1988).
Staba et al., Gene Ther., 5, 293-300 (1998).
Standiford et al., Human Gene Ther., 10, 899-909 (1999).
Wakabayashi et al., Neurol. Med. Chir. (Tokyo), 37, 739-746 (1997).
Weichselbaum et al., Cancer Res., 54, 4266-4269 (1994).
Whartenby et al., Drugs, 50 (6), 951-958 (1995).
Wright et al., Cancer Gene Ther., 5 (6), 371-379 (1998).
Donnelly et al., Radiology, 219 (1), 166-170 (Apr. 2001).
Sharma et al., Hum. Gene Ther., 12, 1109-1131 (Jun. 10, 2001).
Crystal et al., Hum. Gene Ther., 13 (1), 65-100 (Jan. 1, 2002).
Harvey et al., Hum, Gene Ther., 13 (1), 15-63 (Jan. 1, 2002).
Mundt et al., Clin. Cancer Res., 10 (17), 5747-5753 (Sep. 1, 2004).
Senzer et al., J. Clin. Oncol., 22 (4), 592-601 (Feb. 15, 2004).

* cited by examiner

THERAPEUTIC REGIMEN FOR TREATING CANCER COMPRISING THE ADMINISTRATION OF ADENOVIRAL VECTORS COMPRISING A TNF-α TRANSGENE

CROSS-REFERENCE TO RELATED APPLICATION

This patent application is a continuation-in-part of copending U.S. patent application Ser. No. 10/001,017, filed Nov. 2, 2001.

FIELD OF THE INVENTION

This invention pertains to a method and a composition for treating cancer in a human.

BACKGROUND OF THE INVENTION

The desire of cancer research is the identification of a therapy effective on one or several different types of cancers. The American Cancer Society, alone, distributed approximately $1 billion last year to cancer researchers working to elucidate the mechanisms of a multitude of cancer types. Yet, despite extensive research into the disease, effective cancer therapeutics remain elusive for the medical community. Clinicians have realized limited success with the current standard therapies: chemotherapy, radiation therapy, and surgery. However, each therapy has inherent limitations. Chemotherapy and radiation therapy cause extensive damage to normal, healthy tissue, despite efforts to target such therapy to abnormal tissue (e.g., tumors). Surgery can be effective in removing masses of cancerous cells; however, even the most talented surgeon cannot ensure complete removal of affected tissue nor are all tumors in an anatomical location amenable to surgical removal. The limitations of existing therapies are reflected in the 60% 5-year relative survival rate for all cancers combined (*Cancer Facts & Figures* 2001, The American Cancer Society, New York, N.Y.).

Clinicians have looked to the delivery of therapeutic nucleic acid sequences as a possible alternative to existing cancer therapies. The local production of therapeutic agents at biologically-significant levels in target sites in vivo, thereby reducing the toxicity to normal tissues, addresses some of the limitations associated with conventional therapy. Numerous genes have been examined for anti-tumor effects. One of the most promising anti-tumor agents is tumor necrosis factor (TNF), in particular TNF-α, which has displayed activity with respect to a number of cancer cell lines. TNF-α is a 17 kDa polypeptide secreted by macrophages and monocytes. TNF-α has been shown to selectively destroy tumor vasculature and activate a myriad of immune cells, as well as induce apoptosis of some tumor cell types (Baher et al., *Anticancer Research*, 19, 2917–2924 (1999), and Mauceri et al., *C. R. Acad. Sci. III*, 322, 225–228 (1998)). However, the use of TNF in humans as an anti-cancer agent has been limited by its severe systemic effects, including hypotension and respiratory insufficiency (Mauceri et al., supra). In addition, many cancer types are refractory to treatment with TNF-α protein such as, for instance, pancreatic cancer (Brown et al., *J. Immunotherapy*, 10, 376–378 (1991)), gastric cancer (Muggia, *Anticancer Drugs*, 3, 211–217 (1992)), metastatic breast cancer (Budd et al., *Cancer*, 68, 1694–1695 (1991)), and colorectal cancer (Heim et al., *Onkologie*, 13, 444–447 (1990)).

Accordingly, there remains a need for a composition suitable for use in treating a variety of cancer types in a patient, as well as a method for delivering the composition to treat cancer. In particular, there remains a need for a composition and method that optimizes the local effects of anti-cancer agents, such as TNF, while minimizing toxicity. The invention provides such a composition and method. These and other advantages of the invention, as well as additional inventive features, will be apparent from the description of the invention provided herein.

BRIEF SUMMARY OF THE INVENTION

The invention provides a method of treating cancer in a human. The method comprises administering to a human a dose of a pharmaceutical composition comprising (i) a pharmaceutically acceptable carrier and (ii) an adenoviral vector comprising a nucleic acid sequence encoding TNF-α operably linked to a promoter, wherein the dose comprises about $1 \times 10^7$ to about $4 \times 10^{12}$ particle units (pu) of adenoviral vector, at least once in a therapeutic period comprising up to about 10 weeks. The method preferably further comprises administering a dose of ionizing radiation over the duration of the therapeutic period, whereby the cancer in human is treated. The pharmaceutical composition is preferably administered directly to the tumor, e.g., by multiple injections to different points of the tumor.

The invention further provides a method of treating a human for multiple tumors, wherein the method comprises contacting a first tumor with a dose of the pharmaceutical composition at least once in a therapeutic period comprising up to about 10 weeks, whereby the human is treated for the first tumor and one or more additional tumors.

DETAILED DESCRIPTION OF THE INVENTION

Figure 1:
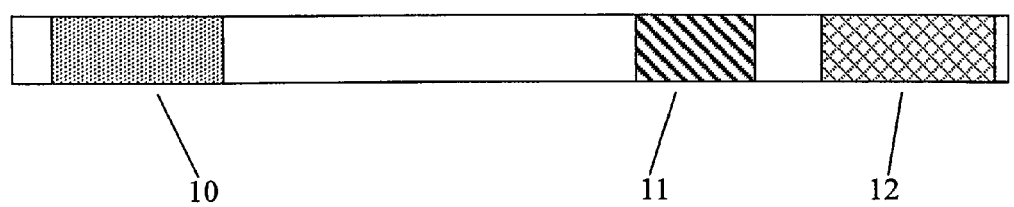
FIG. 1 is a schematic representation of an unmodified adenoviral vector genome.

The invention provides a method of treating cancer in a human (e.g., a patient in need of such treatment). The method preferably involves the delivery of TNF-α to a tumor, preferably directly to the tumor, in combination with radiation therapy, whereby the size of the tumor is reduced. In particular, the method comprises administering to a human in need of treatment a pharmaceutical composition comprising an adenoviral vector, preferably a replication-deficient adenoviral vector, comprising a nucleic acid sequence encoding TNF-α in a pharmaceutically acceptable carrier. The method preferably further comprises administering a dose of ionizing radiation to the human. The delivery of the TNF-α coding sequence, especially in combination with the delivery of radiation, offers an improvement over previously described treatments using soluble TNF protein by optimizing local effect and minimizing systemic toxicity. Indeed, the invention is predicated, in part, on the surprising discovery that tumor size can be reduced without significant toxicity to the patient. In addition, the inventive method has been demonstrated to reduce the size of tumors that were refractory to treatment with TNF-α protein. Various aspects of the inventive method are discussed below. Although each parameter is discussed separately, the inventive method comprises combinations of the parameters set forth below to treat a human for cancer. Accordingly, any combination of parameters can be used according to the inventive method.

Adenoviral Vector

The inventive method comprises administering to a human a pharmaceutical composition comprising an adenoviral vector comprising a nucleic acid sequence encoding TNF-α in a pharmaceutically acceptable carrier. Adenovirus (Ad) is a 36 kb double-stranded DNA virus that efficiently transfers DNA in vivo to a variety of different target cell types. The vector can be produced in high titers and can efficiently transfer DNA to replicating and non-replicating cells. Any subtype, mixture of subtypes, or chimeric adenovirus can be used as the source of the viral genome for the adenoviral vector. Adenoviral stocks that can be employed as a source of adenovirus can be amplified from the adenoviral serotypes 1 through 51, which are currently available from the American Type Culture Collection (ATCC, Manassas, Va.), or from any other serotype of adenovirus available from any other source. For instance, an adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 8, 9, 10, 13, 15, 17, 19, 20, 22–30, 32, 33, 36–39, and 42–47), subgroup E (serotype 4), subgroup F (serotypes 40 and 41), or any other adenoviral serotype. Preferably, the adenoviral vector is of subgroup C, especially serotype 2 or 5.

The adenoviral vector comprising a nucleic acid sequence encoding TNF-α is ideally manipulated to limit replication of the vector within the target tissue. For example, the adenoviral vector of the pharmaceutical composition can be a conditionally-replicating adenoviral vector, which is engineered to replicate under conditions pre-determined by the practitioner. For example, replication-essential gene functions, e.g., gene functions encoded by the adenoviral early regions, can be operably linked to an inducible, repressible, or tissue-specific transcription control sequence, e.g., promoter. In this embodiment, replication requires the presence or absence of specific factors that interact with the transcription control sequence. Replication of the adenoviral vector can be limited to a target tissue, thereby allowing greater distribution of the vector throughout the tissue while exploiting adenovirus' natural ability to lyse cells during the replication cycle, thereby providing an additional mode of destroying tumor cells. Conditionally-replicating adenoviral vectors are described further in U.S. Pat. No. 5,998,205.

Preferably, the adenoviral vector is replication-deficient. By "replication-deficient" is meant that the adenoviral vector comprises a genome that lacks at least one replication-essential gene function. A deficiency in a gene, gene function, or gene or genomic region, as used herein, is defined as a deletion of sufficient genetic material of the viral genome to impair or obliterate the function of the gene whose nucleic acid sequence was deleted in whole or in part. Replication-essential gene functions are those gene functions that are required for replication (e.g., propagation) and are encoded by, for example, the adenoviral early regions (e.g., the E1, E2, and E4 regions), late regions (e.g., the L1–L5 regions), genes involved in viral packaging (e.g., the IVa2 gene), and virus-associated RNAs (e.g., VA-RNA1 and/or VA-RNA-2). Preferably, the replication deficient adenoviral vector comprises an adenoviral genome deficient in at least one replication-essential gene function of one or more regions of the adenoviral genome. Preferably, the adenoviral vector is deficient in at least one gene function of the E1 region of the adenoviral genome required for viral replication (denoted an E1-deficient adenoviral vector). In addition to such a deficiency in the E1 region, the recombinant adenovirus also can have a mutation in the major late promoter (MLP), as discussed in International Patent Application WO 00/00628. More preferably, the vector is deficient in at least one replication-essential gene function of the E1 region and at least part of the nonessential E3 region (e.g., an Xba I deletion of the E3 region) (denoted an E1/E3-deficient adenoviral vector). With respect to the E1 region, the adenoviral vector can be deficient in at least part of the E1A region and at least part of the E1B region, e.g., in at least one replication-essential gene function of each of the E1A and E1B regions.

Preferably, the adenoviral vector is "multiply deficient," meaning that the adenoviral vector is deficient in one or more gene functions required for viral replication in each of two or more regions of the adenoviral genome. For example, the aforementioned E1-deficient or E1/E3-deficient adenoviral vector can be further deficient in at least one replication-essential gene function of the E4 region (denoted an E1/E4-deficient adenoviral vector). An adenoviral vector deleted of the entire E4 region can elicit a lower host immune response.

Alternatively, the adenoviral vector is deficient in at least one gene function of the E1 region and is deficient in at least one gene function of the E2 region (denoted an E1/E2-deficient adenoviral vector). If the adenoviral vector of the present invention is deficient in a replication-essential gene function of the E2A region, the vector preferably does not comprise a complete deletion of the E2A region, which is less than about 230 base pairs in length. Generally, the E2A region of the adenovirus codes for a DBP (DNA binding protein), a polypeptide required for DNA replication. DBP is composed of 473 to 529 amino acids depending on the viral serotype. It is believed that DBP is an asymmetric protein that exists as a prolate ellipsoid consisting of a globular Ct with an extended Nt domain. Studies indicate that the Ct domain is responsible for DBP's ability to bind to nucleic acids, bind to zinc, and function in DNA synthesis at the level of DNA chain elongation. However, the Nt domain is believed to function in late gene expression at both transcriptional and post-transcriptional levels, is responsible for efficient nuclear localization of the protein, and also may be involved in enhancement of its own expression. Deletions in the Nt domain between amino acids 2 to 38 have indicated that this region is important for DBP function (Brough et al., Virology, 196, 269–281 (1993)). While deletions in the E2A region coding for the Ct region of the DBP have no effect on viral replication, deletions in the E2A region which code for amino acids 2 to 38 of the Nt domain of the DBP impair viral replication. It is preferable that any multiply replication-deficient adenoviral vector contain this portion of the E2A region of the adenoviral genome. In particular, for example, the desired portion of the E2A region to be retained is that portion of the E2A region of the adenoviral genome which is defined by the 5' end of the E2A region, specifically positions Ad5(23816) to Ad5(24032) of the E2A, region of the adenoviral genome of serotype Ad5. This portion of the adenoviral genome desirably is included in the adenoviral vector because it is not complemented in current E2A cell lines so as to provide the desired level of viral propagation.

In a particularly preferred embodiment, the adenoviral vector comprises an adenoviral genome deficient in one or more replication-essential gene functions of each of the E1 and E4 regions (i.e., the adenoviral vector is an E1/E4-deficient adenoviral vector), preferably with the entire coding region of the E4 region having been deleted from the adenoviral genome. In other words, all the open reading frames (ORFs) of the E4 region have been removed. The E4 region of the adenoviral vector preferably retains the native E4 promoter, polyadenylation sequence, and/or the right-side inverted terminal repeat (ITR).

The adenoviral vector, when multiply replication-deficient, especially in replication-essential gene functions of the E1 and E4 regions, preferably includes a spacer element to provide viral growth in a complementing cell line similar to that achieved by singly replication-deficient adenoviral vectors, particularly an adenoviral vector comprising a deficiency in the E1 region. The spacer element can contain any sequence or sequences which are of a desired length, such as sequences at least about 15 base pairs (e.g., between about 15 base pairs and about 12,000 base pairs), preferably about 100 base pairs to about 10,000 base pairs, more preferably about 500 base pairs to about 8,000 base pairs, even more preferably about 1,500 base pairs to about 6,000 base pairs, and most preferably about 2,000 to about 3,000 base pairs in length. The spacer element sequence can be coding or non-coding and native or non-native with respect to the adenoviral genome, but does not restore the replication-essential function to the deficient region. In the absence of a spacer, production of fiber protein and/or viral growth of the multiply replication-deficient adenoviral vector is reduced by comparison to that of a singly replication-deficient adenoviral vector. However, inclusion of the spacer in at least one of the deficient adenoviral regions, preferably the E4 region, can counteract this decrease in fiber protein production and viral growth. The use of a spacer in an adenoviral vector is described in U.S. Pat. No. 5,851,806.

The adenoviral vector can be deficient in replication-essential gene functions of only the early regions of the adenoviral genome, only the late regions of the adenoviral genome, and both the early and late regions of the adenoviral genome. The adenoviral vector also can have essentially the entire adenoviral genome removed, in which case it is preferred that at least either the viral inverted terminal repeats (ITRs) and one or more promoters or the viral ITRs and a packaging signal are left intact (i.e., an adenoviral amplicon). The larger the region of the adenoviral genome that is removed, the larger the piece of exogenous nucleic acid sequence that can be inserted into the genome. For example, given that the adenoviral genome is 36 kb, by leaving the viral ITRs and one or more promoters intact, the exogenous insert capacity of the adenovirus is approximately 35 kb. Alternatively, a multiply deficient adenoviral vector that contains only an ITR and a packaging signal effectively allows insertion of an exogenous nucleic acid sequence of approximately 37–38 kb (in that adenovirus can package DNA up to about 105% the size of the wild-type adenoviral genome). Of course, the inclusion of a spacer element in any or all of the deficient adenoviral regions will decrease the capacity of the adenoviral vector for large inserts. Suitable replication-deficient adenoviral vectors, including multiply deficient adenoviral vectors, are disclosed in U.S. Pat. Nos. 5,851,806 and 5,994,106 and International Patent Applications WO 95/34671 and WO 97/21826. An especially preferred adenoviral vector for use in the present inventive method is that described in International Patent Application PCT/US01/20536.

In the preferred E1/E4-deficient adenoviral vector for use in the inventive method, the L5 fiber region is retained, and a spacer is located between the L5 fiber region and the right-side ITR. More preferably, in such an adenoviral vector, the E4 polyadenylation sequence alone or, most preferably, in combination with another sequence, exists between the L5 fiber region and the right-side ITR, so as to sufficiently separate the retained L5 fiber region from the right-side ITR, such that viral production of such a vector approaches that of a singly replication-deficient adenoviral vector, particularly an E1-deficient adenoviral vector.

The spacer element inserted into the adenoviral genome can contain a promoter-variable expression cassette, which can include any promoter (cellular or viral), foreign nucleic acid sequence, and/or polyadenylation sequence. Preferably, in the case of a spacer element inserted into the E4 region (coding sequences for which have been removed), both the E4 polyadenylation sequence and the E4 promoter remain in the vector. In such an embodiment, the spacer element is located between the E4 polyadenylation site and the E4 promoter, or, if the E4 promoter is not present in the vector, the spacer element is proximal to the right-side (3') ITR.

The spacer element can comprise any suitable polyadenylation sequence. Examples of suitable polyadenylation sequences include synthetic optimized sequences, as well as the polyadenylation sequences of BGH (Bovine Growth Hormone), polyoma virus, TK (Thymidine Kinase), EBV (Epstein Barr Virus), and the papillomaviruses, including human papillomaviruses and BPV (Bovine Papilloma Virus). Preferably, the spacer element includes an SV40 (Human Sarcoma Virus-40) polyadenylation sequence. The SV40 polyadenylation sequence allows for higher virus production levels of multiply deficient adenoviral vectors. If the spacer element comprises all or part of a coding sequence and production of a gene product is not desired, the spacer element can be flanked by polyadenylation sequences.

A foreign coding sequence also can function as the spacer element in the E4-deficient region of the adenoviral genome. The foreign coding sequence is limited only by the size of the insert the vector can accommodate and can be any suitable coding sequence. Examples of suitable foreign coding sequences include, but are not limited to, coding sequences encoding marker proteins such as pGUS, secretory alkaline phosphatase, luciferase, β-galactosidase, and human anti-trypsin; therapeutic factors; potential immune modifiers such as B3-19K, E3-14.7, ICP47, fas ligand, and CTLA4; biologically inactive sequences (e.g., sequences that are (i) not transcribed to produce a product or (ii) encode a defective or biologically inactive product), and other innocuous sequences such as the glucuronidase gene.

It should be appreciated that the deletion of different regions of the adenoviral vector can alter the immune response of the mammal. In particular, the deletion of different regions can reduce the inflammatory response generated by the adenoviral vector. Furthermore, the adenoviral vector's coat protein can be modified so as to decrease the adenoviral vector's ability or inability to be recognized by a neutralizing antibody directed against the wild-type coat protein, as described in International Patent Application WO 98/40509.

Similarly, the coat protein of the adenoviral vector can be manipulated to alter the binding specificity or recognition of the adenoviral vector for a viral receptor on a potential host cell. Such manipulations can include deletion of regions of the fiber, penton, hexon, pIIIa, pVI, and/or pIX, insertions of various native or non-native ligands into portions of the coat protein, and the like. Manipulation of the coat protein can broaden the range of cells infected by the adenoviral vector or enable targeting of the adenoviral vector to a specific cell type.

For example, in one embodiment, the adenoviral vector comprises a chimeric coat protein (e.g., a fiber, hexon, pIX, pIIIa, or penton protein), which differs from the wild-type (i.e., native) coat protein by the introduction of a nonnative amino acid sequence, preferably at or near the carboxyl terminus. Preferably, the nonnative amino acid sequence is inserted into or in place of an internal coat protein sequence. The nonnative amino acid sequence can be inserted within the internal coat protein sequence or at the end of the internal coat protein sequence. The resultant chimeric viral coat protein is able to direct entry into cells of the adenoviral vector comprising the coat protein that is more efficient than entry into cells of an adenoviral vector that is identical except for comprising a wild-type viral coat protein rather than the chimeric viral coat protein. Preferably, the chimeric coat protein binds a novel endogenous binding site present on the cell surface that is not recognized, or is poorly recognized, by an adenoviral vector comprising a wild-type coat protein. One direct result of this increased efficiency of entry is that the adenoviral vector can bind to and enter cell types which an adenovirus comprising wild-type coat protein typically cannot enter or can enter with only a low efficiency. If desired, native binding of the adenoviral coat proteins, e.g., the fiber or penton base, can be ablated.

In another embodiment, the adenoviral vector comprises a chimeric virus coat protein not selective for a specific type of eukaryotic cell. The chimeric coat protein differs from the wild-type coat protein by an insertion of a nonnative amino acid sequence into or in place of an internal coat protein sequence. For example, a ligand comprising about five to about nine lysine residues (preferably seven lysine residues) is attached to the C-terminus of the adenoviral fiber protein via a non-coding spacer sequence. In this embodiment, the chimeric virus coat protein efficiently binds to a broader range of eukaryotic cells than a wild-type virus coat, such as described in International Patent Application WO 97/20051. In that a tumor does not comprise a homogenous population of cancer cells, such adenoviral vectors are particularly preferred.

The specificity of binding of the adenoviral vector to a given cell also can be adjusted by use of an adenovirus comprising a short-shafted adenoviral fiber gene, as discussed in U.S. Pat. No. 5,962,311. Use of an adenovirus comprising a short-shafted adenoviral fiber gene reduces the level or efficiency of adenoviral fiber binding to its cell-surface receptor and increases adenoviral penton base binding to its cell-surface receptor, thereby increasing the specificity of binding of the adenoviral vector to a given cell. Alternatively, use of an adenovirus comprising a short-shafted fiber enables targeting of the adenovirus to a desired cell-surface receptor by the introduction of a nonnative amino acid sequence either into the penton base or the fiber knob.

Of course, the ability of an adenoviral vector to recognize a potential host cell can be modulated without genetic manipulation of the coat protein, i.e., through use of a bi-specific molecule. For instance, complexing an adenovirus with a bispecific molecule comprising a penton base-binding domain and a domain that selectively binds a particular cell surface binding site enables the targeting of the adenoviral vector to a particular cell type.

Suitable modifications to an adenoviral vector are described in U.S. Pat. Nos. 5,559,099, 5,731,190, 5,712,136, 5,770,442, 5,846,782, 5,926,311, 5,965,541, 6,057,155, 6,127,525, and 6,153,435 and International Patent Applications WO 96/07734, WO 96/26281, WO 97/20051, WO 98/07865, WO 98/07877, WO 98/54346, WO 00/15823, and WO 01/58940. The construction of adenoviral vectors is well understood in the art. Adenoviral vectors can be constructed and/or purified using the methods set forth, for example, in U.S. Pat. No. 5,965,358 and International Patent Applications WO 98/56937, WO 99/15686, and WO 99/54441. Moreover, numerous adenoviral vectors are available commercially.

Replication-deficient adenoviral vectors are typically produced in complementing cell lines that provide gene functions not present in the replication-deficient adenoviral vectors, but required for viral propagation, at appropriate levels in order to generate high titers of viral vector stock. A preferred cell line complements for at least one and preferably all replication-essential gene functions not present in a replication-deficient adenovirus. The complementing cell line can complement for a deficiency in at least one replication-essential gene function encoded by the early regions, late regions, viral packaging regions, virus-associated RNA regions, or combinations thereof, including all adenoviral functions (e.g., to enable propagation of adenoviral amplicons). Most preferably, the complementing cell line complements for a deficiency in at least one replication-essential gene function (e.g., two or more replication-essential gene functions) of the E1 region of the adenoviral genome, particularly a deficiency in a replication-essential gene function of each of the E1A and E1B regions. In addition, the complementing cell line can complement for a deficiency in at least one replication-essential gene function of the E2 (particularly as concerns the adenoviral DNA polymerase and terminal protein) and/or E4 regions of the adenoviral genome. Desirably, a cell that complements for a deficiency in the E4 region comprises the E4-ORF6 gene sequence and produces the E4-ORF6 protein. Such a cell desirably comprises at least ORF6 and no other ORF of the E4 region of the adenoviral genome. The cell line preferably is further characterized in that it contains the complementing genes in a non-overlapping fashion with the adenoviral vector, which minimizes, and practically eliminates, the possibility of the vector genome recombining with the cellular DNA. Accordingly, the presence of replication competent adenoviruses (RCA) is minimized if not avoided in the vector stock, which, therefore, is suitable for certain therapeutic purposes, especially gene therapy purposes. The lack of RCA in the vector stock avoids the replication of the adenoviral vector in non-complementing cells. Construction of such a complementing cell lines involve standard molecular biology and cell culture techniques, such as those described by Sambrook et al., *Molecular Cloning, a Laboratory Manual*, 2d edition, Cold Spring Harbor Press, Cold Spring Harbor, N.Y. (1989), and Ausubel et al., *Current Protocols in Molecular Biology*, Greene Publishing Associates and John Wiley & Sons, New York, N.Y. (1994). Complementing cell lines for producing the gene transfer vector (e.g., adenoviral vector)

include, but are not limited to, 293 cells (described in, e.g., Graham et al., *J. Gen. Virol.*, 36, 59–72 (1977)), PER.C6 cells (described in, e.g., International Patent Application WO 97/00326, and U.S. Pat. Nos. 5,994,128 and 6,033,908), and 293-ORF6 cells (described in, e.g., International Patent Application WO 95/34671 and Brough et al., *J. Virol.*, 71, 9206–9213 (1997)). In some instances, the complementing cell will not complement for all required adenoviral gene functions. Helper viruses can be employed to provide the gene functions in trans that are not encoded by the cellular or adenoviral genomes to enable replication of the adenoviral vector.

Nucleic Acid Sequence Encoding TNF

The adenoviral vector, preferably the replication-deficient adenoviral vector, comprises a nucleic acid sequence encoding TNF-$\alpha$. While other members of the TNF family of proteins, such as Fas ligand and CD40 ligand, have utility in treating a number of diseases, TNF-$\alpha$ has been proven to be an effective anti-cancer agent. The effect of TNF-$\alpha$ on cancer is multifactorial including the induction of apoptosis and tumor necrosis. Indirect systemic effects of TNF-$\alpha$ include activation of immune effector cells including induction of cytokine secretion and activation of the vascular coagulation system. TNF-$\alpha$ induces adhesiveness of vascular endothelium to neutrophils and platelets and decreases thrombomodulin production (Koga et al., *Am. J. Physiol.*, 268, 1104–1113 (1995)). The result is clot formation in the tumor neovasculature and subsequent hemorrhagic necrosis of the tumors. A nucleic acid sequence encoding TNF-$\alpha$ is described in detail in U.S. Pat. No. 4,879,226.

While it is preferred that the nucleic acid sequence encoding TNF-$\alpha$ is that set forth in U.S. Pat. No. 4,879,226, many modifications and variations of the nucleic acid sequence are possible and appropriate in the context of the invention. For example, the degeneracy of the genetic code allows for the substitution of nucleotides throughout polypeptide coding regions, as well as in the translational stop signal, without alteration of the encoded polypeptide. Such substitutable sequences can be deduced from the known amino acid sequence of the TNF-$\alpha$ or nucleic acid sequence encoding TNF-$\alpha$ and can be constructed by conventional synthetic or site-specific mutagenesis procedures. Synthetic DNA methods can be carried out in substantial accordance with the procedures of Itakura et al., *Science*, 198, 1056–1063 (1977), and Crea et al., *Proc. Natl. Acad. Sci. USA*, 75, 5765–5769 (1978). Site-specific mutagenesis procedures are described in Maniatis et al., *Molecular Cloning: A Laboratory Manual*, Cold Spring Harbor, N.Y. (2d ed. 1989).

In addition, a nucleic acid sequence encoding a homolog of TNF-$\alpha$, i.e., any protein that is more than about 70% identical (preferably more than about 80% identical, more preferably more than about 90% identical, and most preferably more than about 95% identical) to the protein at the amino acid level and displays the same level of anti-cancer activity of TNF-$\alpha$, can be incorporated into the adenoviral vector (e.g., replication-deficient adenoviral vector). The degree of amino acid identity can be determined using any method known in the art, such as the BLAST sequence database. Furthermore, a homolog of the protein can be any peptide, polypeptide, or portion thereof, which hybridizes to the protein under at least moderate, preferably high, stringency conditions, and retains anti-cancer activity. Exemplary moderate stringency conditions include overnight incubation at 37° C. in a solution comprising 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37–50° C., or substantially similar conditions, e.g., the moderately stringent conditions described in Sambrook et al., supra. High stringency conditions are conditions that use, for example (1) low ionic strength and high temperature for washing, such as 0.015 M sodium chloride/0.0015 M sodium citrate/0.1% sodium dodecyl sulfate (SDS) at 50° C., (2) employ a denaturing agent during hybridization, such as formamide, for example, 50% (v/v) formamide with 0.1% bovine serum albumin (BSA)/0.1% Ficoll/0.1% polyvinylpyrrolidone (PVP)/50 mM sodium phosphate buffer at pH 6.5 with 750 mM sodium chloride, 75 mM sodium citrate at 42° C., or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at (i) 42° C. in 0.2×SSC, (ii) at 55° C. in 50% formamide and (iii) at 55° C. in 0.1×SSC (preferably in combination with EDTA). Additional details and an explanation of stringency of hybridization reactions are provided in, e.g., Ausubel et al., supra.

The nucleic acid sequence can encode a functional portion of TNF-$\alpha$, i.e., any portion of the protein that retains the biological activity of the naturally occurring, full-length protein at measurable levels. A functional TNF-$\alpha$ fragment produced by expression of the nucleic acid sequence of the adenoviral vector, preferably the replication-deficient adenoviral vector, can be identified using standard molecular biology and cell culture techniques, such as assaying the biological activity of the fragment in human cells transiently transfected with a nucleic acid sequence encoding the protein fragment.

Alternatively, the nucleic acid sequence encoding TNF-$\alpha$ can be manipulated to alter (preferably enhance) the activity of the TNF-$\alpha$. The nucleic acid sequence can be manipulated to enhance secretion of the TNF-$\alpha$ protein, or can be manipulated to encode a TNF-$\alpha$ protein that remains bound to the cell surface. The nucleic acid sequence can be manipulated to enhance the stability of the TNF-$\alpha$ protein (e.g., retain proper three-dimensional conformation under adverse conditions), or to increase the potency of the TNF-$\alpha$ protein for activation the TNF receptor. As such, the invention is not limited to that nucleic acid sequence specifically in U.S. Pat. No. 4,879,226, and modifications of the nucleic acid sequence are contemplated herein.

Figure 2:
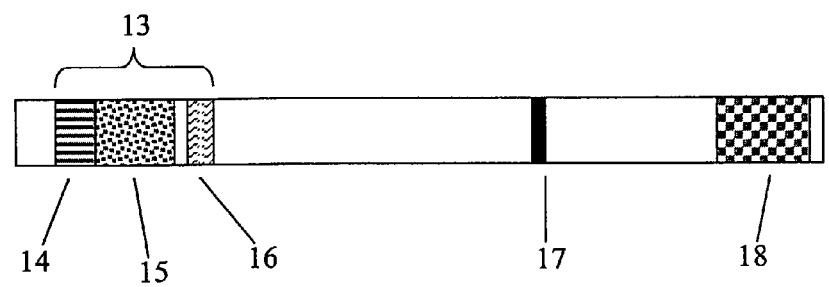
FIG. 2 is a schematic representation of an adenoviral vector containing a modified adenoviral genome and genetic elements in accordance with one embodiment of the present invention.

The nucleic acid sequence is desirably present as part of an expression cassette, i.e., a particular base sequence that possesses functions which facilitate subcloning and recovery of a nucleic acid sequence (e.g., one or more restriction sites) or expression of a nucleic acid sequence (e.g., polyadenylation or splice sites). The nucleic acid sequence coding for TNF-$\alpha$ is preferably located in the E1 region (e.g., replaces the E1 region in whole or in part) of the adenoviral genome. For example, the E1 region can be replaced by a promoter-variable expression cassette comprising a nucleic acid sequence encoding TNF-$\alpha$, as shown in, for example, FIGS. 1 and 2, which depict an unmodified and modified adenoviral vector genome, respectively. The E1 region (10) can be replaced by an expression cassette (13) comprising a radiation-inducible promoter (14), a nucleic acid sequence encoding TNF-$\alpha$ (15), and a polyadenylation sequence (16). The expression cassette is preferably inserted in a 3'-5' orientation, e.g., oriented such that the direction of transcription of the expression cassette is opposite that of the surrounding adenoviral genome. In addition to the expression cassette comprising the nucleic acid sequence encoding TNF-α, the adenoviral vector can comprise other expression cassettes containing nucleic acid sequences encoding other products, which cassettes can replace any of the deleted regions of the adenoviral genome. The insertion of an expression cassette into the adenoviral genome (e.g., the E1 region of the genome) can be facilitated by known methods, for example, by the introduction of a unique restriction site at a given position of the adenoviral genome. As set forth above, preferably the E3 region of the adenoviral vector (11) is deleted (17), and the E4 region (12) is replaced by a spacer element (18).

Preferably, the nucleic acid sequence encoding TNF-α further comprises a transcription-terminating region such as a polyadenylation sequence located 3' of TNF-α coding sequence (in the direction of transcription of the coding sequence). Any suitable polyadenylation sequence can be used, including a synthetic optimized sequence, as well as the polyadenylation sequence of BGH (Bovine Growth Hormone), polyoma virus, TK (Thymidine Kinase), EBV (Epstein Barr Virus), and the papillomaviruses, including human papillomaviruses and BPV (Bovine Papilloma Virus). A preferred polyadenylation sequence is the SV40 (Human Sarcoma Virus-40) polyadenylation sequence.

Preferably, the nucleic acid sequence encoding TNF-α is operably linked to (i.e., under the transcriptional control of) one or more promoter and/or enhancer elements, for example, as part of a promoter-variable expression cassette. Techniques for operably linking sequences together are well known in the art. Any suitable promoter or enhancer sequence can be used in the context of the invention. Suitable viral promoters include, for instance, cytomegalovirus (CMV) promoters, such as the CMV immediate-early promoter (described in, for example, U.S. Pat. No. 5,168,062), promoters derived from human immunodeficiency virus (HIV), such as the HIV long terminal repeat promoter, Rous sarcoma virus (RSV) promoters, such as the RSV long terminal repeat, mouse mammary tumor virus (MMTV) promoters, HSV promoters, such as the Lap2 promoter or the herpes thymidine kinase promoter (Wagner et al., *Proc. Natl. Acad. Sci.*, 78, 144–145 (1981)), promoters derived from SV40 or Epstein Barr virus, an adeno-associated viral promoter, such as the p5 promoter, and the like. The regulatory sequences to which the nucleic acid sequence is operably linked also can comprise a tissue-specific promoter, i.e., a promoter that is preferentially activated in a given tissue and results in production of a gene product, particularly TNF-α, in the tissue where activated. For example, regulatory sequences selectively active in, for instance, endothelial cells or stromal cells are ideal for expressing an exogenous nucleic acid sequence in the environment of cancer cells.

Many of the above-described promoters are constitutive promoters. Instead of being a constitutive promoter, the promoter can be an inducible promoter, i.e., a promoter that is up- and/or down-regulated in response to an appropriate signal. For example, an expression control sequence up-regulated by a chemotherapeutic agent is particularly useful in cancer applications (e.g., a chemo-inducible promoter). In addition, an expression control sequence can be up-regulated by a radiant energy source or by a substance that distresses cells. For example, an expression control sequence can be up-regulated by ultrasound, light activated compounds, radiofrequency, chemotherapy, and cyofreezing. A preferred adenoviral vector according to the invention comprises a chemo-inducible or radiation-inducible promoter operably linked to the nucleic acid sequence encoding TNF-α. The use of a radiation-inducible promoter enables localized control of TNF-α production, for example, by the administration of radiation to a cell or host comprising the adenoviral vector, thereby minimizing systemic toxicity. Any suitable radiation-inducible promoter can be used in the context of the invention. A preferred radiation-inducible promoter for use in the context of the invention is the early growth region-1 (EGR-1) promoter, specifically the CArG domain of the EGR-1 promoter. The region of the EGR-1 promoter likely responsible for radiation-inducibility is located between nucleotides −550 bp and −50 bp. The EGR-1 promoter is described in detail in U.S. Pat. No. 5,206,152 and International Patent Application WO 94/06916. Another suitable radiation-inducible promoter is the c-Jun promoter, which is activated by X-radiation. The region of the c-Jun promoter likely responsible for radiation-inducibility is believed to be located between nucleotides −1.1 kb to 740 bp. The c-Jun promoter and the EGR-1 promoter are further described in, for instance, U.S. Pat. No. 5,770,581. The promoter can be introduced into the adenoviral genome by any suitable method, such as by use of a unique restriction site in a given region of the adenoviral genome. Alternatively, the promoter can be inserted as part of the expression cassette comprising the nucleic acid sequence encoding TNF-α.

Other Adenoviral Vector Considerations

The adenoviral vector described can comprise nucleic acid sequences other than that encoding TNF-α, e.g., a nucleic acid sequence to treat other similar or different diseases and/or afflictions including, but not limited to, chronic lung diseases, such as emphysema, asthma, adult respiratory distress syndrome, and chronic bronchitis, as well as coronary heart disease, common complications associated with cancer, and other afflictions suitably treated or prevented by gene therapy, vaccination, and the like. If the additional nucleic acid sequence (i.e., transgene) confers a prophylactic or therapeutic benefit, the nucleic acid sequence can exert its effect at the level of RNA or protein. Alternatively, the additional nucleic acid sequence can encode an antisense molecule, a ribozyme, a protein that affects splicing or 3' processing (e.g., polyadenylation), or a protein that affects the level of expression of another gene within the cell (i.e., where gene expression is broadly considered to include all steps from initiation of transcription through production of a processed protein), such as by mediating an altered rate of mRNA accumulation or transport or an alteration in post-transcriptional regulation. The additional nucleic acid sequence can encode a chimeric protein for combination therapy. The additional nucleic acid sequence also can encode a factor that acts upon a different target than TNF-α, thereby providing multifactorial cancer treatment. Alternatively, the additional nucleic acid sequence can encode a factor that enhances the effect of TNF-α. An example of such a factor is PKR, double-stranded RNA dependent protein kinase, which renders cancer cells more prone to apoptosis (see, for example, U.S. Pat. No. 5,976,800).

The adenoviral vector can comprise an additional nucleic acid sequence encoding an anti-angiogenic substance other than TNF-α. An anti-angiogenic substance is any biological factor that prevents or ameliorates neovascularization. The anti-angiogenic substance can effect partial or complete prevention and amelioration of angiogenesis to achieve a therapeutic effect. An anti-angiogenic substance includes, for instance, an anti-angiogenic factor, an anti-sense molecule specific for an angiogenic factor, a ribozyme, a receptor for an angiogenic factor, and an antibody that binds a receptor for an angiogenic factor. To prevent vascular leakage into surrounding tissue, which can lead to tumor spread, the adenoviral vector can comprise an additional nucleic acid sequence that encodes a vessel maturation factor, such as, for example, an angiopoietin (Ang, e.g., Ang-1 and Ang-2), midkine (MK), COUP-TFII, and heparin-binding neurotrophic factor (HBNF, also known as heparin binding growth factor). A nucleic acid sequence encoding an immunosuppressor also can be incorporated into the adenoviral vector to reduce any inappropriate immune response thereto as a result of administering the adenoviral vector to a host.

The adenoviral vector can further comprise a nucleic acid sequence encoding a cytokine, such as an interferon (INF $\alpha$, $\beta$, $\gamma$), a colony stimulating factor, or an interleukin (IL-1, IL-2, IL-3, IL-10, IL-12, IL-13, IL-15, etc.). The additional nucleic acid sequence can encode a pro-drug converting enzyme, such as HSV thymidine kinase (see, for example, International Patent Application WO 01/24684). The additional nucleic acid sequence preferably encodes a protein that is deleterious to the cancer cells of a mammal (i.e., a "deleterious protein"). Nucleic acid sequences that encode proteins that are deleterious to cancer cells are known in the art, examples of which include nucleic acid sequences that encode p53, Fas, Fas ligand (FasL), FasLM45 (a derivative of FasL that has a deletion in the protease cleavage site), Fas-associating protein with death domain (FADD; also known as mediator of receptor-induced toxicity (MORT-1)), a cell death-inducing coding sequence of Bcl-2 which comprises an N-terminal deletion, a cell death-inducing coding sequence of Bcl-x which comprises an N-terminal deletion, caspases (e.g., caspase 1 (interleukin-1 $\beta$-converting enzyme (ICE)), caspase 3, caspase 8 (MACH/FLICE (FADD-homologous ICE-CED3-like protease)/Mch5), and caspase 10 (Mch4)), receptor interacting protein (RIP), cell death abnormal (CED4), Apaf-1, RIP-associated ICH-1/CED-3-homologous protein with a death domain (RAIDD)/caspase and RIP adapter with death domain (CRADD), inhibitor of NF-$\kappa$B (I$\kappa$B), DNA fragmentation factor (DFF), TNF-R1, TNF-related apoptosis-inducing ligand (TRAIL; apo2 ligand (Apo2L)), death receptor 4 (DR4), DR5, bax, bak, bid, bad, bik, bif-2, c-myc, JUN, a dominant negative JUN product, a protease, a protein kinase, a transcriptional activator, a signal transduction protein, protein kinase C, PITSLRE kinase, DAP kinase, JUN N-terminal kinase (JNK)/SAPK, Daxx, ras, Raf, NIK, MEKK1, ASK1, protein kinase R (PKR), Rb194, an adenoviral E1A product, an adenoviral E2F product, a synthetic cell cycle-independent form of an adenoviral E2F product, an adenoviral E4/ORF4 product, apoptin, an apoptotic-active portion of any of the foregoing, and a combination of two or more of the foregoing.

The additional nucleic acid sequence can encode a marker protein, such as green fluorescent protein or luciferase. Such marker proteins are useful in vector construction and determining vector migration. Marker proteins also can be used to determine points of injection in order to efficiently space injections of the pharmaceutical composition to provide a widespread area of treatment. Alternatively, the nucleic acid sequence can encode a selection factor (e.g., an antibiotic resistance factor), which also is useful in vector construction protocols. If desired, the additional nucleic acid sequence(s) can be part of an expression cassette(s).

Any of the nucleic acid sequences described herein can be altered from their native form to increase their therapeutic effect. For example, a cytoplasmic form of a therapeutic gene product can be converted to a secreted form by incorporating a signal peptide into the encoded gene product. A gene product also can be engineered to be taken up by neighboring cells by fusion of the peptide with VP22.

Pharmaceutical Composition

The pharmaceutical composition of the invention comprises a pharmaceutically acceptable carrier and the adenoviral vector (e.g., a replication-deficient adenoviral vector) comprising the nucleic acid sequence encoding TNF-$\alpha$. Any suitable pharmaceutically acceptable carrier can be used within the context of the invention, and such carriers are well known in the art. The choice of carrier will be determined, in part, by the particular site to which the pharmaceutical composition is to be administered and the particular method used to administer the pharmaceutical composition.

Suitable formulations include aqueous and non-aqueous solutions, isotonic sterile solutions, which can contain antioxidants, buffers, bacteriostats, and solutes that render the formulation isotonic with the blood or other bodily fluid of the intended recipient, and aqueous and non-aqueous sterile suspensions that can include suspending agents, solubilizers, thickening agents, stabilizers, and preservatives. Preferably, the pharmaceutically acceptable carrier is a liquid that contains a buffer and a salt. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the pharmaceutically acceptable carrier is a buffered saline solution.

More preferably, the pharmaceutical composition is formulated to protect the adenoviral vector from damage prior to administration. The particular formulation desirably decreases the light sensitivity and/or temperature sensitivity of the adenoviral vector. Indeed, the pharmaceutical composition will be maintained for various periods of time and, therefore should be formulated to ensure stability and maximal activity at the time of administration. Typically, the pharmaceutical composition is maintained at a temperature above 0° C., preferably at 4° C. or higher (e.g., 4–10° C.). In some embodiments, it is desirable to maintain the pharmaceutical composition at a temperature of 10° C. or higher (e.g., 10–20° C.), 20° C. or higher (e.g., 20–25° C.), or even 30° C. or higher (e.g., 30–40° C.). The pharmaceutical composition can be maintained at the aforementioned temperature(s) for at least 1 day (e.g., 7 days (1 week) or more), though typically the time period will be longer, such as at least 3, 4, 5, or 6 weeks, or even longer, such as at least 10, 11, or 12 weeks, prior to administration to a patient. During that time period, the adenoviral gene transfer vector optimally loses no, or substantially no, activity, although some loss of activity is acceptable, especially with relatively higher storage temperatures and/or relatively longer storage times. Preferably, the activity of the adenoviral vector composition decreases about 20% or less, preferably about 10% or less, and more preferably about 5% or less, after any of the aforementioned time periods.

To this end, the pharmaceutical composition preferably comprises a pharmaceutically acceptable liquid carrier, such as, for example, those described above, and a stabilizing agent selected from the group consisting of polysorbate 80, L-arginine, polyvinylpyrrolidone, $\alpha$-D-glucopyranosyl $\alpha$-D-glucopyranoside dihydrate (commonly known as trehalose), and combinations thereof. More preferably, the stabilizing agent is trehalose, or trehalose in combination with polysorbate 80. The stabilizing agent can be present in any suitable concentration in the pharmaceutical composition. When the stabilizing agent is trehalose, the trehalose desirably is present in a concentration of about 2–10% (wt./vol.), preferably about 4–6% (wt./vol.) of the pharmaceutical composition. When trehalose and polysorbate 80 are present in the pharmaceutical composition, the trehalose preferably is present in a concentration of about 4–6% (wt./vol.), more preferably about 5% (wt./vol.), while the polysorbate 80 desirably is present in a concentration of about 0.001–0.01% (wt./vol.), more preferably about 0.0025% (wt./vol.). When a stabilizing agent, e.g., trehalose, is included in the pharmaceutical composition, the pharmaceutically acceptable liquid carrier preferably contains a saccharide other than trehalose. Suitable formulations of the pharmaceutical composition are further described in U.S. Pat. No. 6,225,289 and International Patent Application WO 00/34444.

The pharmaceutical composition can further be formulated to reduce adherence loss of the adenoviral vector on devices used to prepare, store, or administer the expression vector, such as glassware, syringes, catheters, or needles. Use of such a pharmaceutical composition will extend the shelf life of the pharmaceutical composition, facilitate administration, and increase the efficacy of the inventive method. In this regard, the pharmaceutical composition also can be formulated to enhance the spread of the adenoviral vector throughout the target tissue and/or enhance transduction efficiency. To this end, the pharmaceutical composition also can comprise hyaluronidase, which has been shown to enhance uptake of adenoviral vectors. Addition of proteases to the pharmaceutical composition can enhance the spread of the adenoviral vector throughout the tumor. It is desirable to formulate the composition such that the adenoviral vector (e.g., replication-deficient adenoviral vector) remains in the target tissue and does not leak into surrounding normal tissue, i.e., to increase retention of the pharmaceutical composition in the target tissue. Accordingly, agents that increase viscosity of the pharmaceutical composition, such as stimuli-sensitive polymers, can be included. Alternatively, the adenoviral vectors of the pharmaceutical composition can be bound to biocompatible solid carriers, such as particulate carriers (e.g., beads, wafers, etc.), that remain in the target tissue due to size, or incorporated into a matrix, such as gel or foam.

In addition, the pharmaceutical composition can comprise additional therapeutic or biologically-active agents. For example, therapeutic factors useful in the treatment of a particular indication can be present. Factors that control inflammation, such as ibuprofen or steroids, can be part of the pharmaceutical composition to reduce swelling and inflammation associated with in vivo administration of the adenoviral vector and physiological distress. Immune system suppressors can be administered with the pharmaceutical composition to reduce any immune response to the adenoviral vector itself or associated with a disorder. Alternatively, immune enhancers can be included in the pharmaceutical composition to upregulate the body's natural defenses against disease. Moreover, cytokines other than TNF-α can be administered with the pharmaceutical composition to attract immune effector cells to the tumor site.

Anti-angiogenic factors, such as soluble growth factor receptors (e.g., sflt), growth factor antagonists, i.e., angiotensin, and the like, also can be part of the pharmaceutical composition. Similarly, vitamins and minerals, anti-oxidants, and micronutrients can be co-administered with the pharmaceutical composition. Antibiotics, i.e., microbicides and fungicides, can be present to reduce the risk of infection associated with gene transfer procedures and other disorders. The addition of chemotherapeutic agents to the pharmaceutical composition can provide an additional mechanism of effecting tumor reduction.

Target Tissue

The inventive method can be used to deliver a nucleic acid sequence encoding TNF-α to any target tissue (e.g., tumor tissue) able to be transduced by adenoviral vectors, such as those adenoviral vectors described herein. Preferably, the target tissue comprises TNF-α receptors, such that TNF-α can exert its biological activity on the tissue. Ideally, the target tissue is a tumor, e.g., a solid tumor or a tumor associated with soft tissue (i.e., soft tissue sarcoma), in a human. The tumor can be associated with cancers of (i.e., located in) the oral cavity and pharynx, the digestive system, the respiratory system, bones and joints (e.g., bony metastases), soft tissue, the skin (e.g., melanoma), breast, the genital system, the urinary system, the eye and orbit, the brain and nervous system (e.g., glioma), or the endocrine system (e.g., thyroid) and is not necessarily the primary tumor. Tissues associated with the oral cavity include, but are not limited to, the tongue and tissues of the mouth. Cancer can arise in tissues of the digestive system including, for example, the esophagus, stomach, small intestine, colon, rectum, anus, liver, gall bladder, and pancreas. Cancers of the respiratory system can affect the larynx, lung, and bronchus and include, for example, non-small cell lung carcinoma. Tumors can arise in the uterine cervix, uterine corpus, ovary vulva, vagina, prostate, testis, and penis, which make up the male and female genital systems, and the urinary bladder, kidney, renal pelvis, and ureter, which comprise the urinary system. The target tissue also can be associated with lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like).

The tumor can be at any stage, and can be subject to other therapies. The inventive method is useful in treating tumors (i.e., destruction of tumor cells or reduction in tumor size) that have been proven to be resistant to other forms of cancer therapy, such as radiation-resistant tumors. The tumor also can be of any size. Indeed, the invention is predicated, in part, on the surprising ability of the inventive method to significantly reduce the size of initially large tumors (e.g., 42 $cm^2$ or 4400 $cm^3$). Ideally, in treating the human for cancer, the inventive method results in cancerous (tumor) cell death and/or reduction in tumor size. It will be appreciated that tumor cell death can occur without a substantial decrease in tumor size due to, for instance, the presence of supporting cells, vascularization, fibrous matrices, etc. Accordingly, while reduction in tumor size is preferred, it is not required in the treatment of cancer.

Methods of Administration

The inventive method comprises administering the pharmaceutical composition to a human for the treatment of cancer. The use of TNF-α protein in humans as an anti-cancer/anti-tumor agent has been limited by severe systemic effects arising as a result of treatment. Therefore, in order to attenuate or prevent such negative side effects, it is desirable to administer the nucleic acid sequence encoding TNF-α only to the tissue which requires it (i.e., the tumor) or, at the very least, to promote expression of the nucleic acid sequence predominantly in tumor tissue. Accordingly, the pharmaceutical composition can be administered by any means such that TNF-α is produced within, or in close proximity to, the target tissue.

The invention preferably involves contacting target tissue by administering the pharmaceutical composition comprising the adenoviral vector (e.g., the replication-deficient adenoviral vector) comprising a nucleic acid sequence encoding TNF-α in a localized manner to the target tissue. While any suitable means of administering the pharmaceutical composition to the tumor can be used within the context of the invention, preferably localized administration to the tumor is accomplished by directly injecting the pharmaceutical composition comprising the adenoviral vector comprising the nucleic acid sequence encoding TNF-α into a tumor. By the term "injecting," it is meant that the pharmaceutical composition is forcefully introduced into the target tissue.

The pharmaceutical composition is desirably administered in a uniform manner across the tumor mass. Thus, when administering the pharmaceutical composition via injection, the injection is performed to maximize distribution throughout the tumor. For example, the needle of the injection device punctures the surface of the tumor tissue (commonly at a depth of about 1 cm to about 5 cm, preferably about 2 cm to about 4 cm (e.g., 3 cm) depending on tumor volume), and the pharmaceutical composition is expelled from the delivery device as the needle is slowly removed from the tissue, such that vector is released along the track of the needle. In addition, timing of each injection can be controlled to evenly deliver the pharmaceutical composition to the tumor. In other words, the pharmaceutical composition can be expelled from the injection device slowly (e.g., about 5 seconds per injection, preferably about 10 seconds per injection, and more preferably about 15 seconds per injection) for efficient uptake of the adenoviral vector by the surrounding tissue. In one embodiment, from about 1 µl to about 10 µl of pharmaceutical composition is administered to the tumor over 10 minutes. Alternatively, the pharmaceutical composition can be quickly and forcefully expelled from the injection device (e.g., in a "spray") in order to force vector uptake. Indeed, the pharmaceutical composition can be administered such that the pharmaceutical composition transverses normal tissue prior to contacting target tissue. Of course, homogenous distribution of the pharmaceutical composition across the target tissue is not required.

In instances wherein a tumor is not readily visible through the skin, a clinician can use medical equipment to visualize the tumor, estimate tumor volume, and guide injection placement. Imaging technology for cancer diagnosis is quite advanced. Ultrasound and computed tomography (CT) equipment are commonly used to detect tumor masses. However, more advanced imaging techniques have been developed and include positron emission tomography (PET), which reveals the metabolic activity of tissues, single photon emission computed tomography (SPECT), spiral CT, magnetic resonance imaging (MRI), and endoscopic ultrasonography, which employs a fiber-optic endoscope fitted with a probe.

Any suitable injection device can be used within the context of the invention. For example, the common medical syringe can be used to directly inject the pharmaceutical composition into a subcutaneous tumor. Of course, standard medical syringes can be used to inject target tissue (e.g., tumors) not directly beneath the skin. If the tumor is not readily accessible, the tumor can be exposed during a surgical procedure to allow injection. However, minimally invasive delivery devices allow administration of the pharmaceutical composition without invasive medical procedures. Such devices are capable of accessing target tissues not directly accessible through the skin, for example, via small incisions of less than 5 inches. Minimally invasive injection devices can comprise injector tips which are flexible and steerable to allow access via small incisions to the curved outer surface of an organ, e.g., the liver. An alternative means of non-invasive injection comprises the use of a needleless injection device, such as the Biojector 2000 Needle-Free Injection Management System® available from Bioject, Inc. The pharmaceutical composition can be administered to a target tissue using a catheter. For example, transcatheter chemoembolization involves insertion of a catheter into the target tissue through a small incision in the skin. Angiography is used to guide the catheter into the vasculature feeding the target tissue, whereupon the therapeutic agent is released together with particulate matter that blocks the flow of blood to the target tissue. The therapeutic agent does not escape into surrounding tissues, and the tumor is starved from nutrients. Endoscopy is similar to catheterization while permitting visualization of the target tissue while administering the pharmaceutical composition. Catheters are useful in both releasing the pharmaceutical composition in to the blood stream that feeds the tumor, as well as injecting the pharmaceutical composition into tumor tissue. To allow for multiple injections with a specific geometry, a marking system can be employed so that the sites of previous injections are well delineated. Enhanced tumor and injection visualization is especially warranted when the pharmaceutical composition is administered to tumor tissue via multiple applications in a distinct geometrical pattern.

In addition to directly injecting the pharmaceutical composition into tumor tissue, the pharmaceutical composition can be topically applied to tumor tissue. For example, the tumor tissue can be bathed in the pharmaceutical composition, thereby effecting gene transfer to the tissue surface and surrounding environment. Of course, more than one route of administration can be used such that, for example, the pharmaceutical composition is injected and topically administered to a tumor tissue. Topical administration comprising bathing the tumor in the pharmaceutical composition allows exposure of the relevant tissue to the adenoviral vector for a longer period of time than commonly allowed by injection. Exposure of the tissue to the pharmaceutical composition for a prolonged period of time can increase the level of uptake in target cells and supporting cells. Likewise, the target tissue can be perfused with the pharmaceutical composition over a period of time using any suitable delivery device, e.g., a catheter. A tumor can be perfused with the pharmaceutical composition over any period of time so long as transduction occurs, e.g., from about 1 minute to about 20 hours (e.g., from about 1 minute to about 12 hours), preferably from about 15 minutes to about 10 hours (e.g., from about 15 minutes to about 6 hours), more preferably from about 30 minutes to about 5 hours (e.g., from about 30 minutes to about 3 hours), and more preferably from about 1–2 hours.

While less preferred, other routes of administration can be used to administer the pharmaceutical composition. Indeed, although more than one route can be used to administer the pharmaceutical composition, a particular route can provide a more immediate and more effective reaction than another route. For example, while not particularly preferred, the pharmaceutical composition can be applied or instilled into body cavities, absorbed through the skin, inhaled, or administered parenterally via, for instance, intramuscular, intravenous, peritoneal, or intraarterial administration. Preferably, the adenoviral vector of the pharmaceutical composition parenterally administered to a patient is specifically targeted to particular cells, e.g., cancer cells. For regional delivery, the pharmaceutical composition can be administered intraarterially or intravenously, e.g., via the hepatic artery for delivery to the liver or the carotid artery for delivery to the brain. For administration to the brain, the pharmaceutical composition can be introduced into tumor tissue using an intratumoral delivery catheter, ventricular shunt catheter attached to a reservoir (e.g., Omaya reservoir), infusion pump, or introduced into a tumor resection cavity (such as Gliasite, Proxima Therapeutics). Tumor tissue in the brain also can be contacted by administering the pharmaceutical composition via convection using a continuous infusion catheter or through cerebrospinal fluid. Alternatively, the pharmaceutical composition can be administered to the pleural cavity for delivery to the lung or the peritoneal cavity for mesothelioma. In addition, the lymphatic system can be accessed, for example, following intratumoral injection, for delivery to lymph nodes. For regional delivery, the pharmaceutical composition is preferably delivered directly into an artery feeding the target tissue. As discussed herein, an adenoviral vector can be modified to alter the binding specificity or recognition of the adenoviral vector for a receptor on a potential host cell. With respect to adenovirus, such manipulations can include deletion of regions of the fiber, penton, or hexon, insertions of various native or non-native ligands into portions of the coat protein, and the like. Parenteral administration can require large doses or multiple administrations to effectively deliver the adenoviral vector of the pharmaceutical composition to the appropriate host cells.

In some instances, the pharmaceutical composition need not contact the target tissue directly to realize a therapeutic effect. For example, the pharmaceutical composition can be administered to supporting tissue, whereby either the adenoviral vector or resulting TNF-α is transmitted to target tissue wherein it exerts its biologic effect. For example, it has been surprisingly observed that the administration of the pharmaceutical composition directly to tumor tissue in accordance with the inventive method can promote treatment lesions located in other regions of the body. In other words, delivery of the pharmaceutical composition to a tumor can promote regression of additional (i.e., one or more other) tumors located elsewhere in the body, e.g., metastasis. Accordingly, the inventive method can treat a human for multiple (i.e., two or more) tumors, preferably by reducing the size of multiple tumors in the human body. In particular, multiple tumors located in different regions of the body (e.g., a first tumor in the shoulder and a second tumor in the abdomen) can be treated by delivery of the pharmaceutical composition to a first tumor. In this embodiment, the pharmaceutical composition is administered to a first tumor, which allows treatment of the first tumor and, additionally, one or more other tumors which were not directly administered the pharmaceutical composition. Preferably, tumor cells within the first tumor and one or more additional tumors are destroyed. Also preferably, the size of the first tumor and one or more additional tumors is reduced. A systemic biological effect can, therefore, be achieved via local (direct) or regional delivery (e.g., delivery directly into the regional lymph or blood supply) of the pharmaceutical composition.

The pharmaceutical composition can be administered in or on a device that allows controlled or sustained release of the adenoviral vector, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the adenoviral vector. The pharmaceutical composition of the inventive method also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

The pharmaceutical composition also can be incorporated into or coat other materials, such as glass or magnetic beads, that are subsequently administered to a patient. For example, the FDA has approved study of the use of radioactive glass beads to deliver concentrated radiation therapy to hidden tissues (e.g., invasive cancers, tumors deep within the body cavity, etc.). Such beads can contain or be coated with the pharmaceutical composition. Alternatively, magnetic beads coated with the pharmaceutical composition can be administered to a patient, and directed to target tissue by placement of a magnet in the vicinity of a tumor. While beads are likely to remain lodged in the body unless forcibly removed, biodegradable delivery devices dissolve into non-toxic end products that are naturally removed from the body. The Gliadel® wafer, for example, is currently used to deliver chemotherapeutic drugs to the site of glioblastoma. Such biodegradation matrices, once implanted, can release the adenoviral vector encoding TNF-α through degradation of the matrix, thereby delivering the therapeutic agent to the relevant site without clinician intervention.

Multiple Applications of a Single Dose

While administration of a dose of the pharmaceutical composition can be accomplished through a single application (e.g., a single injection or a single topical application to the target tissue), preferably a single dose is administered via multiple applications of the pharmaceutical composition to different points of the target tumor. The multiple applications can number anywhere from about 2 applications to about 50 applications or more (including all integers between 2 and 50), depending on the size and location of the tumor. For example, a single dose can be administered to relevant tissue in 40 separate injections or more. A single dose of pharmaceutical composition preferably is administered in 2, 3, 4, 5, 6, 7, 8, 9, 10 or more applications (e.g., 15, 20, 25, 30, 35, 40, or 45 applications), more preferably about 2–8 applications, and even more preferably about 2–5 applications. The number of applications depends on the tumor location, tumor size, tumor type, and the like. For example, if administering to soft tissue sarcoma, which is typically very large (e.g., 78 cm in its largest dimension), the single dose preferably is administered in about 3–8 applications. For smaller or more compact solid tumors, only 2–5 applications are preferred. Multiple applications provide an advantage over single applications in that they can be manipulated by such parameters as a specific geometry defined by the location on the tumor where each application is administered. The administration of a single dose of the pharmaceutical composition is better controlled using multiple applications, and the effectiveness with which any given dose is administered can be maximized. In this way, too, the adenoviral vector and, ultimately TNF-α production, can be uniformly distributed throughout the tumor.

The specific geometry of the multiple applications is defined by the location on the target tissue, either in two- or three-dimensional space, where each application of the pharmaceutical composition is administered. The location of each application will be dictated by tumor type and volume. The pattern of applications is selected to effect a broad distribution of the replication-deficient adenoviral vector and, ultimately, the produced TNF-α protein, to the tumor. With respect to the specific geometry of the multiple applications in two-dimensional space, the specific geometry is defined by a plane (i.e., a cross-section of the target tissue) in which the multiple applications lie. The plane defined by the multiple applications can lie at a constant distance from the surface of the target tissue (i.e., substantially parallel to the surface of the target tissue), or, alternatively, the plane can lie at an angle with respect to the surface of the target tissue. Furthermore, the multiple applications can define any suitable pattern or specific geometry. Therefore, for example, in two-dimensional space, the multiple applications can define a square whereas in three-dimensional space the multiple applications can define a cube. In that the inventive method comprises multiple rounds of therapy (i.e., administration of multiple doses of the pharmaceutical composition over a period of time (therapeutic period), as discussed below), the geometry of the multiple applications desirably is rotated or shifted to achieve maximal distribution of the pharmaceutical composition over the therapeutic period. To aid in consistent, patterned application of the pharmaceutical composition, a grid or template overlay will aid in guiding injections, marking devices can record previous injection points, and imaging techniques can be used to visualize the target tissue.

Figure 3A:
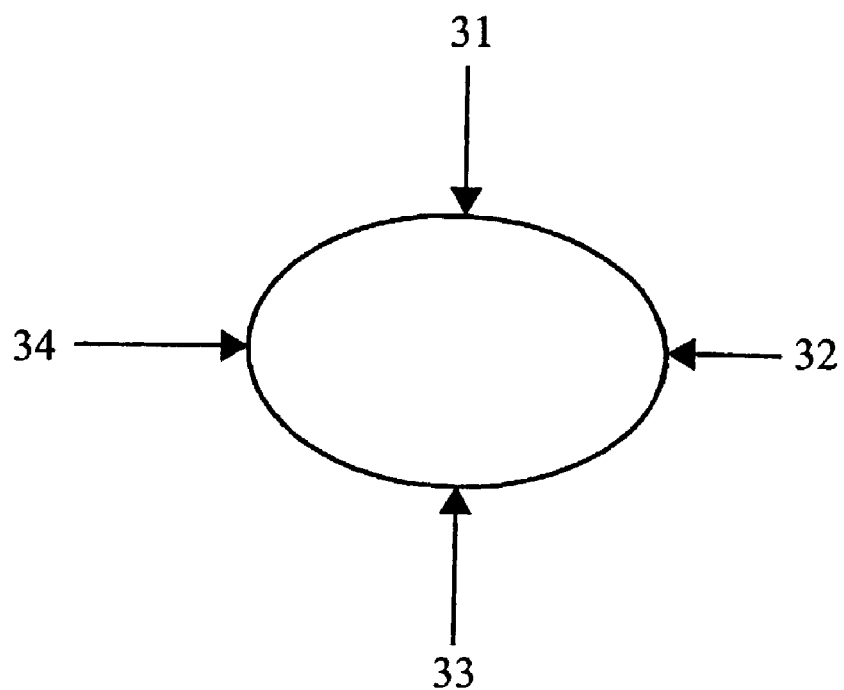
FIG. 3A is an end-on view of a solid tumor with an illustration of a preferred pattern for multiple applications of a single dose of pharmaceutical composition to the solid tumor.
Figure 3B:
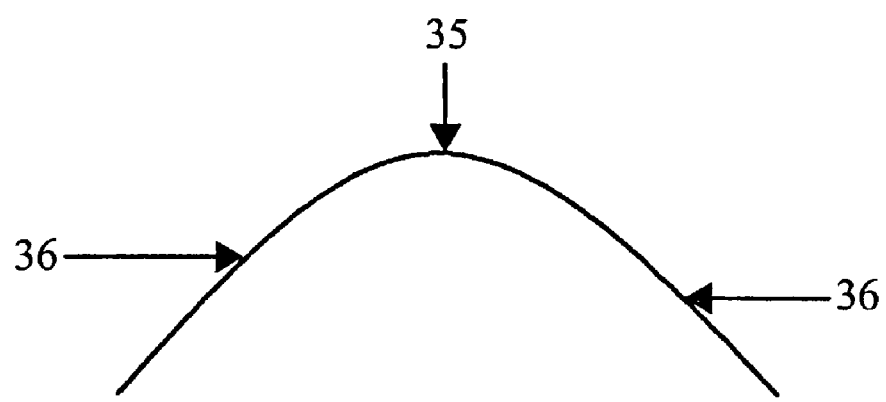
FIG. 3B is a side-view of a solid tumor with an illustration of a preferred pattern for multiple applications of a single dose of pharmaceutical composition to the solid tumor.

When administering the pharmaceutical composition directly to a solid tumor, a single dose of pharmaceutical composition preferably is administered via multiple applications around the circumference of the tumor, especially wherein the administration device, e.g., a needle, is inserted to a depth of about 1 cm to about 5 cm in the tumor mass, preferably at a depth of about 2 cm to about 4 cm (e.g., about 3 cm). Ideally, the multiple applications are administered to the tumor at equally spaced intervals around the periphery (circumference), e.g., in a clockwise or counter-clockwise pattern (e.g., at the 12 o'clock, 3 o'clock, 6 o'clock, and 9 o'clock positions), and an anterior-posterior or dorsal-caudal position, as illustrated in FIG. 3A and FIG. 3B, which depict an end-on view and side-view of a solid tumor, respectively, with an illustration of a preferred pattern for multiple applications of a single dose of pharmaceutical composition to the solid tumor. The geometry of the multiple applications is then shifted in subsequent dose administrations. For example, in an especially preferred embodiment, the inventive method comprises administering the pharmaceutical composition in the following pattern: (a) 12 o'clock (31), 3 o'clock (32), 6 o'clock (33), and 9 o'clock (34) positions and an anterior-posterior or dorsal-caudal position (35) for each administration in week 1, (b) 1 o'clock, 4 o'clock, 7 o'clock, and 10 o'clock positions and an anterior-posterior or dorsal-caudal position for the first administration in week 2, (c) 2 o'clock, 5 o'clock, 8 o'clock, and 11 o'clock positions and an anterior-posterior or dorsal-caudal position for the second administration in week 2, and (d) repeating (a)–(c) around the periphery of the tumor, using parallel injections (36), with each subsequent dose administration.

Figure 4:
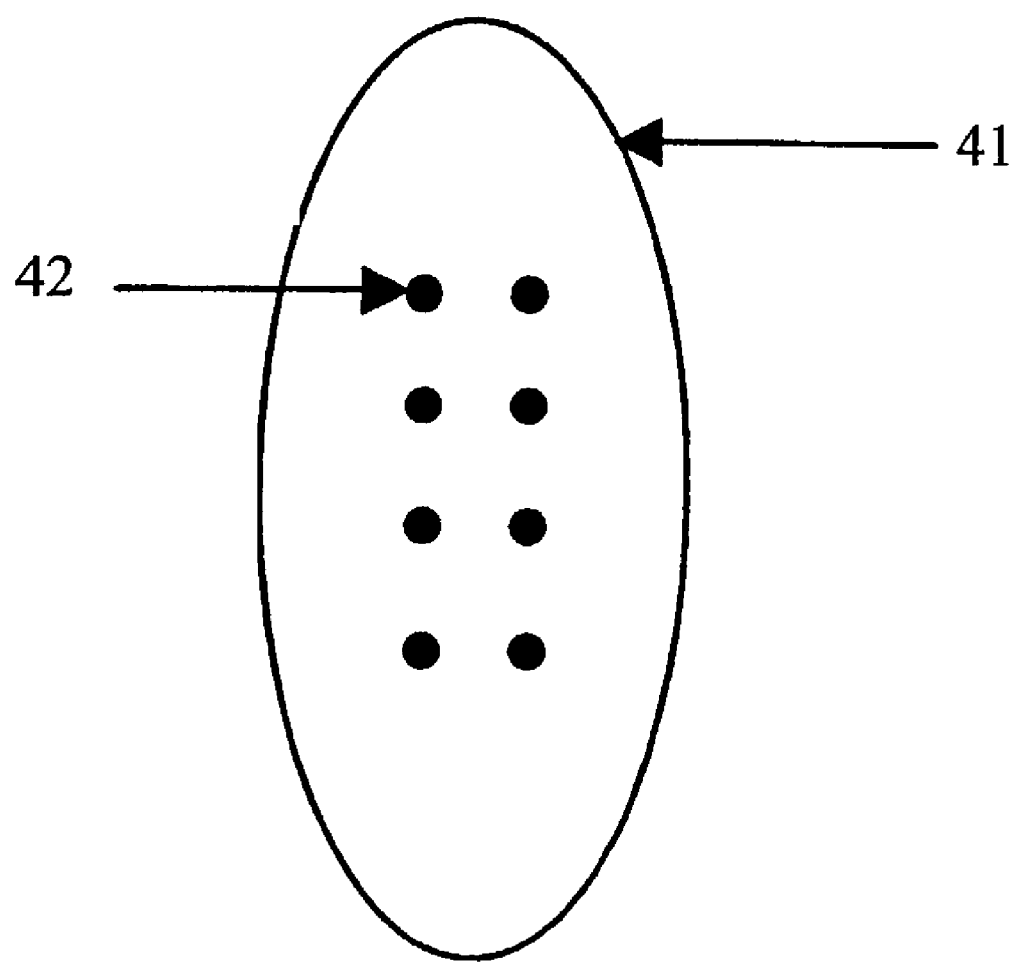
FIG. 4 is an end-on view of a soft tissue sarcoma with an illustration of a preferred pattern for multiple applications of a single dose of pharmaceutical composition to the soft tissue sarcoma.

When administering the pharmaceutical composition to a diffuse or large tumor, such as that associated with soft tissue sarcoma, injection into the circumference of the tumor is not possible. Accordingly, the injections are administered in a pattern comprising a series of parallel lines, as illustrated in FIG. 4, which depicts an end-on view of a soft tissue sarcoma (41) with an illustration of a preferred pattern for multiple applications (42) of a single dose of pharmaceutical composition to the soft tissue sarcoma. Alternatively, the injections can be administered in concentric circles. In either case, the specific geometry of applications is selected with the goal of widespread delivery of the adenoviral vector (e.g., replication-deficient adenoviral vector). In some embodiments, a dose of pharmaceutical composition is not administered directly to the tumor tissue, but is locally administered to the surrounding cells/tissue of the tumor, to prevent tumor spread.

Another parameter of the multiple applications which can be manipulated is the time differential between each application. Preferably, each of the multiple applications is administered within about 10 minutes (e.g., about 0.5–10 minutes) of each other, more preferably within about 8 minutes (e.g., about 1–8 minutes) of each other, and even more preferably within about 6 minutes (e.g., about 3–6 minutes) of each other. Most preferably, all of the multiple applications of the single dose are administered within the aforesaid time frames.

Dosage

The dose of the pharmaceutical composition, and particularly the amount of the adenoviral vector comprising the nucleic acid sequence encoding TNF-α, will depend on a number of factors, including tumor size, the extent of any side-effects, the particular route of administration, and the like. The dosage should be such that the negative side-effects associated with TNF-α are minimized. Desirably, a single dose of the pharmaceutical composition comprises at least about $1 \times 10^5$ particles (which also is referred to as particle units) to at least about $1 \times 10^{13}$ particles of the adenoviral vector. The dose preferably is at least about $1 \times 10^6$ particles (e.g., about $4 \times 10^6$–$4 \times 10^{12}$ particles), more preferably at least about $1 \times 10^7$ particles, more preferably at least about $1 \times 10^8$ particles (e.g., about $4 \times 10^8$–$4 \times 10^{11}$ particles), and most preferably at least about $1 \times 10^9$ particles to at least about $1 \times 10^{10}$ particles (e.g., about $4 \times 10^9$–$4 \times 10^{10}$ particles) of the adenoviral vector. Alternatively, the dose of the pharmaceutical composition comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ particles). In other words, a single dose of pharmaceutical composition can comprise about $1 \times 10^6$ particle units (pu), $4 \times 10^6$ pu, $1 \times 10^7$ pu, $4 \times 10^7$ Pu, $1 \times 10^8$ pu, $4 \times 10^8$ pu, $1 \times 10^9$ pu, $4 \times 10^9$ pu, $1 \times 10^{10}$ pu, $4 \times 10^{10}$ pu, $1 \times 10^{11}$ pu, $4 \times 10^{11}$ pu, $1 \times 10^{11}$ pu, $4 \times 10^{11}$ pu, $1 \times 10^{12}$ pu, or $4 \times 10^{12}$ pu of the adenoviral vector (e.g., the replication-deficient adenoviral vector). Each application of a multiple application protocol for a single dose will include the approximate fraction of the total such that the aggregation of the individual applications equals a single dose as described above. Thus, if there are five applications of a dose of the pharmaceutical composition, the amount of adenoviral vector (e.g., the replication-deficient adenoviral vector) in each application is desirably one-fifth of a single dose as described above.

The dose as described herein is suitable for a volume of targeted tissue of about 3 cm$^2$ to about 300 cm$^2$ (e.g., about 5 cm$^2$, 7 cm$^2$, 8 cm$^2$, or 9 cm$^2$), typically about 10 cm$^2$ to about 200 cm$^2$ (e.g., about 15 cm$^2$, 20 cm$^2$, 25 cm$^2$, 30 cm$^2$, 35 cm$^2$, 40 cm$^2$, 45 cm$^2$, or 50 cm$^2$), more typically about 50 cm$^2$ to about 125 cm$^2$ (e.g., 75 cm$^2$, 80 cm$^2$, 85 cm$^2$, 90 cm$^2$, or 110 cm$^2$), although tumors smaller than 3 cm$^2$ or larger than 300 cm$^2$ can be treated with the inventive method. When injecting the pharmaceutical composition directly into a target tissue, a single application can comprise about 100 µl to about 20 ml of the pharmaceutical composition, preferably about 250 µl to about 10 ml, more preferably about 500 µl to about 5 ml (e.g., 1 ml, 2 ml, or 3 ml). Ideally, when administering multiple applications of a single dose via injection, each application contains about 1 ml of pharmaceutical composition.

Thus, in a single dose of the pharmaceutical composition involving, for example, an E1A/E1B/E3/E4-deficient adenoviral vector comprising the nucleic acid sequence encoding human TNF-α under the control of EGR-1 promoter (such as that described in International Patent Application WO 02/00906), about $1\times10^8$–$1\times10^{12}$ adenoviral particles are administered to a tumor with an estimated volume of about 3 cm$^2$ to about 150 cm$^2$. Under these conditions, a substantial level of TNF-α production is achieved in the target tissue without producing the negative side effects associated with systemic administration of the TNF-α protein.

Radiation Therapy

A typical course of treatment for most types of cancer is radiation therapy. Radiation therapy uses a beam of high-energy particles or waves, such as X-rays and gamma rays, to eradicate cancer cells by inducing mutations in cellular DNA. In that cancer cells divide more rapidly than normal cells, tumor tissue is more susceptible to radiation than normal tissue. Radiation also has been shown to enhance exogenous DNA expression in exposed cells. In a preferred embodiment, the inventive method further comprises administering a dose of radiation to a patient over the therapeutic period. Intratumoral delivery of the nucleic acid sequence encoding TNF-α and confocal radiation to the tumor site results in localized delivery of two potent anti-cancer treatment modalities. When the nucleic acid sequence encoding TNF-α is operably linked to a radiation-inducible promoter, radiation potentiates TNF-α production and maintains therapeutic levels of TNF-α at the tumor site continuously throughout the period of radiation therapy, in addition to the additive or synergistic effect of radiation and TNF-α observed in eradicating tumor cells (see, for example, Hersh et al., *Gene Therapy*, 2, 124–131 (1995), and Kawashita et al., *Human Gene Therapy*, 10, 1509–1519 (1999)).

Any type of radiation can be administered to a patient, so long as the dose of radiation is tolerated by the patient without significant negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581). The effects of radiation can be at least partially controlled by the clinician. The dose of radiation is preferably fractionated for maximal target cell exposure and reduced toxicity. Radiation can be administered concurrently with radiosensitizers that enhance the killing of tumor cells, or with radioprotectors (e.g., IL-1 or IL-6) that protect healthy tissue from the harmful effects of radiation. Similarly, the application of heat, i.e., hyperthermia, or chemotherapy can sensitize tissue to radiation.

The source of radiation can be external or internal to the patient. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by patients. Internal radiation therapy involves implanting a radiation-emitting source, such as beads, wires, pellets, capsules, and the like, inside the body at or near the tumor site. Such implants can be removed following treatment, or left in the body inactive. Types of internal radiation therapy include, but are not limited to, brachytherapy, interstitial irradiation, and intracavity irradiation. Internal radiotherapy is particularly suited for cancer treatment using adenoviral vectors in that the pharmaceutical composition of the inventive method can be incorporated in or on the implanted structures, thereby allowing administration of two forms of cancer therapy simultaneously. A less common form of internal radiation therapy is radioimmunotherapy wherein tumor-specific antibodies bound to radioactive material is administered to a patient. The antibodies seek out and bind tumor antigens, thereby effectively administering a dose of radiation to the relevant tissue.

No matter the method of administration, the total dose of radiation administered to a patient in the context of the present invention preferably is about 5 Gray (Gy) to about 70 Gy. More preferably, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1–8 weeks). Accordingly, a daily dose of radiation will comprise approximately 1–5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), preferably 1–2 Gy (e.g., 1.5–2 Gy). The daily dose of radiation should be sufficient to induce expression of the nucleic acid sequence if operably linked to a radiation-inducible promoter. If stretched over a period of time, radiation preferably is not administered every day, thereby allowing the patient to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the response of the patient to therapy and any potential side effects. Radiation therapy can be initiated at any time in the therapeutic period. Preferably, radiation is initiated in week 1 or week 2, and is administered for the remaining duration of the therapeutic period. For example, radiation is administered in weeks 1–6 or in weeks 2–6 of a therapeutic period comprising 6 weeks for treating, for instance, a solid tumor. Alternatively, radiation is administered in weeks 1–5 or weeks 2–5 of a therapeutic period comprising 5 weeks.

In some embodiments, such as those instances wherein the nucleic acid sequence encoding TNF-α is operably-linked to a radiation-inducible promoter, the inventive method comprises exposing the tumor to radiation immediately following administration of the pharmaceutical composition in a dose sufficient to upregulate the activity of the promoter, although up to two months can pass between radiation exposure and administration of the pharmaceutical composition. Care should be taken such that wounds resulting from the tumor or administration of the pharmaceutical composition (i.e., ulcers) are healed or shielded from excessive radiation exposure. Desirably, at least one application of radiation is administered on the day the pharmaceutical composition is administered. Most preferably, the target site is exposed to radiation about 30 minutes to about 6 hours (e.g., about 3 hours), preferably about 1–4 hours (e.g., about 1–2 hours), following administration of the pharmaceutical composition, especially when the adenoviral vector (e.g., the replication-deficient adenoviral vector) comprises a nucleic acid sequence encoding TNF-α, which is operably linked to a radiation-inducible promoter, so as to maximally upregulate activity of the radiation-inducible promoter and the consequent production of TNF-α. Of course, when internal sources of radiation are employed, e.g., brachytheraphy or radio-immunotherapy, the exposure time typically will increase, with a corresponding decrease in the intensity of radiation.

Timing of Administration

The proliferative nature of cancer impedes the complete elimination of the disease from the body. No matter the treatment, a single dose of a therapeutic agent is not likely to accomplish a complete anti-cancer effect, as surviving cancer cells replicate quickly. Indeed, as with most chronic diseases, prolonged treatment involving multiple doses of a therapeutic agent may be required. Accordingly, in one embodiment, the inventive method comprises delivering multiple doses of pharmaceutical composition over a period of time (i.e., a therapeutic period).

Two timing issues exist with respect to the invention: the total therapeutic period, in other words, the entire length of time over which treatment occurs, and the time between the administration of the doses of pharmaceutical composition and/or adjuvant therapies. Ideally, the therapeutic period is not longer than about 10 weeks in length, such as a therapeutic period comprising about 1–10 weeks in length, although it can be shorter than 1 week (e.g., 1, 2, 3, 4, 5, or 6 day(s)) or longer than 10 weeks (e.g., 12, 14, 16, or 18 weeks). Preferably, the therapeutic period is from about 2–9 weeks (i.e., about 2, 3, 4, 5, 6, 7, 8, or 9 weeks in length), more preferably about 3–8 weeks (e.g., 4–7 weeks), and most preferably about 5–6 weeks in length. A therapeutic period of 5–7 weeks provides sufficient time to effectively attack the cancer while not being so long as to jeopardize patient compliance.

With respect to the administration of multiple doses of the pharmaceutical composition, preferably a dose is administered about once a week throughout the therapeutic period. The start of therapy can require more frequent dosing, e.g., a single dose is administered two days/week, three days/week, four days/week, five days/week, six days/week, or seven days/week (daily administration). Ideally, at least two doses are administered during week 1 of the therapeutic period and, if necessary, also during week 2. Thereafter, a single dose of the pharmaceutical composition can be administered each remaining week of the therapeutic period. However, as the timing of administrations will rely on several factors, such as tolerance of the patient to the treatment, the extent of the disease, the availability of the clinician, etc., it is acceptable for more than one week to pass between doses. For example, a dose can be administered every 10 days, bi-weekly, every 18 days, tri-weekly, every 25 days, once a month, or bi-monthly. Preferably, the multiple doses of the pharmaceutical composition are administered such that the level of TNF-α remains above background levels during the therapeutic period.

Indeed, the timing of administration is selected such that gene expression (i.e., expression of the TNF-α coding sequence) occurs, and the desired biological effect is realized. Accordingly, the timing of administration can be optimized for reducing a particular tumor type. For instance, if the tumor is large and diffuse, such as soft tissue sarcoma, the therapeutic period desirably comprises up to five weeks, with two doses of pharmaceutical composition administered in week 1, and one dose of the pharmaceutical composition administered in each subsequent week (e.g., weeks 2–5). For smaller, compact solid tumors, the therapeutic period desirably comprises up to six weeks, with two doses of pharmaceutical composition administered in weeks 1–2, and one dose of pharmaceutical composition administered in each subsequent week (e.g., weeks 3–6). In either case, when two doses of pharmaceutical administration are administered in one week, the doses preferably are administered on day 1 and day 4 of treatment.

In some embodiments, it may be advantageous to employ a method of administering the pharmaceutical composition wherein a dose is continuously administered to the target tissue over a prolonged period of time. For example, continuous perfusion of the target tissue with the pharmaceutical composition may be desirable. Accordingly, the inventive method can comprise contacting the target tissue (e.g., tumor) at least once during the therapeutic period. In other words, a single administration of a dose of pharmaceutical composition is delivered over a prolonged period of time such as, for example, 1–10 weeks in length, although it can be shorter than 1 week (e.g., 1 day, 2 days, 3 days, 4 days, 5 days, 6 days, 2 weeks, 3 weeks, 4 weeks, 5 weeks, 6 weeks, 7 weeks, 8 weeks, or 9 weeks) or longer than 10 weeks (e.g., 12, 14, 16, or 18 weeks). Such a delivery strategy can be accomplished through, for instance, incorporation of the pharmaceutical composition in a sustained-release device or reservoir and implantation into the patient.

Other Considerations

The inventive method provides an efficient and safe therapeutic regimen for delivering TNF-α to a human for the prophylactic or therapeutic treatment of disease. Ideally, the inventive method promotes inhibition of tumor cell proliferation, the inhibition of tumor vascularization, the eradication of tumor cells, and/or a reduction in the size of at least one tumor such that a human is treated for cancer. By "treatment of cancer" is meant alleviation of cancer in whole or in part. Several parameters to be considered in administering TNF-α to a human patient using adenoviral-mediated gene transfer are discussed herein. The proper combination of parameters for a particular situation can be established by the clinician. The progress of the inventive method in treating cancer (e.g., reducing tumor size or eradicating cancerous cells) can be ascertained using any suitable method, such as those methods currently used in the clinic to track tumor size and cancer progress. Tumor size can be figured using any suitable technique, such as measurement of dimensions, or estimation of tumor volume using available computer software, such as FreeFlight software developed at Wake Forest University that enables accurate estimation of tumor volume. Tumor size can be determined by tumor visualization using, for example, CT, ultrasound, SPECT, spiral CT, MRI, photographs, and the like. Measurement of tumor size, detection of new tumors, tumor antigens, or markers (e.g., CEA, PSA, or CA-125), biopsy, surgical downstaging, PET scans, and the like can point to the overall progression (or regression) of cancer in a human. Radioimmunodetection (RAID) is used to locate and stage tumors using serum levels of markers (antigens) produced by and/or associated with tumors ("tumor markers"), e.g., carcinembryonic antigen (CEA), and can be useful as both a pre-treatment diagnostic predicate and a post-treatment diagnostic indicator of recurrence. RAID technology in combination with endoscopic detection systems efficiently distinguishes small tumors from surrounding tissue (see, for example, U.S. Pat. No. 4,932,412). Biopsy is particularly useful in detecting the eradication of cancerous cells within a tissue.

Preferably, the inventive method reduces the size of a tumor at least about 5% (e.g., at least about 10%, 15%, 20%, or 25%). More preferably, tumor size is reduced at about 30% (e.g., at least about 35%, 40%, 45%, 50%, 55%, 60% or 65%). Even more preferably, tumor size is reduced at least about 70% (e.g., at least about 75%, 80%, 85%, 90%, or 95%). Most preferably, the tumor is completely eliminated. In addition, tumor size is reduced as a result of the inventive method preferably without significant adverse events in the human. Adverse events are categorized or "graded" by the Cancer Therapy Evaluation Program (CTEP) of the National Cancer Institute (NCI), with Grade 0 representing minimal adverse side effects and Grade 4 representing the most severe adverse events. The NCI toxicity scale (published April 1999) and Common Toxicity Criteria Manual (updated August 1999) is available through the NCI or in the *Investigator's Handbook* for participants in clinical trials of investigational agents sponsored by the Division of Cancer Treatment and Diagnosis, NCI (updated March 1998). Desirably, the inventive method is associated with minimal adverse events, e.g., Grade 0, Grade 1, or Grade 2 adverse events, as graded by the CTEP/NCI. However, as discussed herein, reduction of tumor size, although preferred, is not required in that the actual size of tumor may not shrink despite the eradication of tumor cells. Eradication of cancerous cells is sufficient to realize a therapeutic effect. Likewise, any reduction in tumor size is sufficient to realize a therapeutic effect.

Detection, monitoring, and rating of various cancers in a human are further described in *Cancer Facts and Figures* 2001, American Cancer Society, New York, N.Y., and International Patent Application WO 01/24684. Accordingly, a clinician can use standard tests to determine the efficacy of the various embodiments of the inventive method in treating cancer. However, in addition to tumor size and spread, the clinician also should consider quality of life and survival of the patient in evaluating efficacy of treatment.

The inventive method can be performed in combination with other therapeutic methods to achieve a desired biological effect in a patient. In one embodiment, the pharmaceutical composition is administered before, during, or after surgical resection of a tumor. Complete surgical removal of tumor tissue is often complicated by invasion of the tumor tissue into surrounding tissues and indefinite margins of the mass. As described herein, treatment of a tumor using the inventive method leads to tumor shrinkage, which will facilitate resection. Moreover, post-surgical administration of the pharmaceutical composition (using the inventive method) can eliminate any residual tumor cells.

Like surgical resection, chemotherapy is a standard treatment for most cancer types. Accordingly, the inventive method can be performed in parallel, before, or after chemical-based therapies. Common chemotherapeutics include, but are not limited to, adriamycin, asparaginase, bleomycin, busulphan, cisplatin, carboplatin, carmustine, capecitabine, chlorambucil, cytarabine, cyclophosphamide, camptothecin, dacarbazine, dactinomycin, daunorubicin, dexrazoxane, docetaxel, doxorubicin, etoposide, floxuridine, fludarabine, fluorouracil, gemcitabine, hydroxyurea, idarubicin, ifosfamide, irinotecan, lomustine, mechlorethamine, mercaptopurine, meplhalan, methotrexate, mitomycin, mitotane, mitoxantrone, nitrosurea, paclitaxel, pamidronate, pentostatin, plicamycin, procarbazine, rituximab, streptozocin, teniposide, thioguanine, thiotepa, vinblastine, vincristine, vinorelbine, taxol, transplatinum, 5-fluorouracil, and the like.

The inventive method can be performed alongside hormone therapy, which is the manipulation of hormone levels in the body to treat disease. Many cancers are somehow affected by the levels of hormones in the body and, as such, typical therapeutics associated with hormone therapy, e.g., tamoxifen, work to reduce the level circulating hormones and/or interrupt the binding of hormones to hormone receptors.

Hyperthermia, by definition, is increasing the body's temperature as a means of therapy. Studies show that hyperthermia is an effective adjuvant therapy by enhancing the effects of chemotherapy, radiotherapy, and immunotherapy (Ito et al., *Cancer Gene Therapy*, 8(9), 649–654 (2001)). The temperature of specific region of the body, such as a tumor site, can be raised by a heating device (e.g., a device that emits microwaves) or by administering a toxin to induce fever or inflammation. Particles that are induced to emit heat also can be administered to the patient such that the area of treatment is localized and internal. Magnetic particles have been shown to generate heat under an alternating magnetic field (AMF) by hysteresis loss (Ito et al, supra). Submicron particles such as these can be administered to the target tissue and activated by AMF. If desired, the nucleic acid sequence encoding TNF-α can be operably linked to a promoter responsive to heat or AMF irradiation, thereby providing an additional safety measure in that TNF-α production is localized to target tissue.

The following examples further illustrate the invention but, of course, should not be construed as in any way limiting its scope.

EXAMPLE 1

This example demonstrates the safety and efficacy of the pharmaceutical composition of the present invention comprising (i) a pharmaceutically acceptable carrier and (ii) an adenoviral vector comprising a nucleic acid sequence encoding TNF-α operably linked to a radiation-inducible promoter, wherein the dose comprises from about $4 \times 10^9$ to about $4 \times 10^{11}$ particle units (pu) of adenoviral vector, in a clinically-relevant animal model.

Preclinical toxicology studies were performed in nude mice (nu/nu) bearing a human SQ-20B squamous cell carcinoma zenograft (n=80) and Balb/c mice (n=100). Ten nu/nu mice/sex/group in four groups totaling 80 mice were used in the study. The four groups consisted of: 1) vehicle control, 2) vehicle control plus radiation, 3) pharmaceutical composition comprising $4 \times 10^9$ pu of adenoviral vector plus radiation, and 4) pharmaceutical composition comprising $4 \times 10^{10}$ pu of adenoviral vector plus radiation. Doses of vehicle or pharmaceutical composition comprising adenoviral vectors were administered by intratumoral injection (20 μl into 2 sites, 40 μl total) into established SQ-20B human squamous cell tumors from 0.4 cm to 0.6 cm in diameter. Ten Balb/c mice/sex/group with 5 groups totaling 100 mice also were used in the study. The groups included: 1) vehicle control, 2) vehicle plus radiation control, 3) pharmaceutical composition comprising $4 \times 10^9$ pu of adenoviral vector plus radiation, 4) pharmaceutical composition comprising $4 \times 10^{10}$ pu of adenoviral vector plus radiation, and 5) pharmaceutical composition comprising $4 \times 10^{11}$ pu of adenoviral vector plus radiation. Doses of vehicle or pharmaceutical composition were administered by (i) subcutaneous (s.c.) injection into the right hind limb of each Balb/c mouse or (ii) intratumorally in nu/nu mice on days 0, 3, 7, and 10 in conjunction with radiation doses of 5 Gy/fraction administered daily on Days 0 through 4 and Days 7 through 11 (total dose 50 Gy) starting 4 hr after injection. Radiation was to (i) the right hind limb of Balb/c mice or (ii) the tumor site of nu/nu mice with the rest of the body shielded.

The adenoviral vectors comprised an E1A/E1B/E3/E4-deficient adenoviral serotype 5 viral backbone comprising the coding sequence for human TNF-α located in the E1 region and operably linked to the EGR-1 promoter. The adenoviral vector further comprised a spacer sequence in the E4 region. Clinical cage-side observations, food consumption, hematology and chemistry, and clinical pathology were evaluated. Subjects were necropsied on days 14 and 28.

In addition, a pharmacokinetics study in nude mice (n=33) was performed. The mice were intratumorally injected with a dose of pharmaceutical composition comprising $4\times10^9$ pu of the adenoviral vector on days 0–2 or daily 5 days/week for two weeks, with or without radiation therapy as described above. Subjects were sacrificed on days 3 or 28. TNF-α levels in plasma and tumor tissue were quantified by ELISA.

Doses of up to 350 times the maximum dose recommended for clinical studies (on a per kg weight basis) were well tolerated without significant toxicity. Erythema of the skin at the injection site in all dose groups was observed in both Balb/c and nu/nu mice and is consistent with the erythema reported after s.c. administration of soluble recombinant human TNF in humans. The majority of the other toxicities observed were found in the highest dose group ($4\times10^{11}$ pu) and were independent of radiation. These toxicities consisted of a local reaction including ulceration, alopecia, and skin discoloration. Any observed systemic reactions were statistically significantly different when comparing the treatment group to the vehicle-treated controls; however, the changes in these parameters compared to normal levels were not considered of toxicological significance. No mice died or had significant toxicities when administered pharmaceutical composition comprising $4\times10^9$ or $4\times10^{11}$ pu of adenoviral vector in combination with 50 Gy of radiation. In addition, intratumoral delivery of the pharmaceutical composition in combination with radiation therapy resulted in significant and sustained levels of TNF-α in tumor homogenates without "spill over" into plasma, and demonstrated pronounced anti-neoplastic activity. Indeed, radiation increased intra-tumoral levels of TNF-α 12-fold.

The above-described results demonstrate the safety and efficacy of the inventive pharmaceutical composition and method in animal models deemed in the art as reasonably predictive of success in humans.

EXAMPLE 2

This example illustrates use of the inventive method to therapeutically treat cancer in a human as indicated by size reduction of tumor mass.

Patients with solid tumors accessible for repeated intratumoral injections were selected for treatment using the inventive method. These patients had failed one or more prior therapies. Patients were injected intra-tumorally with a pharmaceutical composition comprising one of five dose levels of the TNF-α coding sequence-containing adenoviral vector described in Example 1 ($4\times10^9$–$4\times10^{11}$ pu in ½ log increments) over a maximum 6-week therapeutic period. Several patients comprised a lesion treated by radiation only, which served as a control. A single dose of pharmaceutical composition was administered via multiple injections to the tumor on day 1 and day 4 of weeks 1 and 2 of the therapeutic period, and once weekly for weeks 3–6. For each dose, the multiple injections were administered in a pattern such that the injections were equally spaced around the periphery of the tumor. For example, injections were administered to the tumor in the following pattern: 12 o'clock, 3 o'clock, 6 o'clock, and 9 o'clock positions and an anterior-posterior or dorsal-caudal position for each administration in week 1, (b) 1 o'clock, 4 o'clock, 7 o'clock, and 10 o'clock positions, and an anterior-posterior or dorsal-caudal position for the first administration in week 2, (c) 2 o'clock, 5 o'clock, 8 o'clock, and 11 o'clock positions, and an anterior-posterior or dorsal-caudal position for the second administration in week 2, and repeating (a)–(c) around the periphery of the tumor with each subsequent dose administration. Concomitant radiation therapy started on week 2 and was administered for five consecutive days, and not administered for two days, for each remaining week of the therapeutic period, achieving a total dose of 30–70 Gy. Tumor size was calculated at the end of treatment and, if possible, 2–3 months post-treatment.

| Patient | Index Cancer | Lesion Site | Tumor Response % change of tumor size | Response Index |
|---|---|---|---|---|
| 1 | NSCLC | Breast | −62% | PR |
| 2 | Breast | Chest Wall | −100% | CR |
| 3 | Pancreas | Pancreas Bed | −62% | PR |
| 4 | Colon | Peritoneum | −17% | SD |
| 5 | Breast | Supraventrical | −23% | SD |
| 6 | Head/Neck | Mandibular | −17% | SD |
| 7 | Rectal | Rectal | −100% | CR |
| 8 | Head/Neck | Head/Neck | Not Evaluable | Not Evaluable |
| 9 | Breast | Breast | Not Evaluable | Not Evaluable |
| 10 | Pancreas | Pancreas | −29 | MR |
| 11 | Colon | Groin | −38 | MR |
| 12 | NSCLC | Supraclavicular | −60 | PR |
| 13 | Melanoma | Axilla | −100 | CR |
| 14 | Sarcoma | Skin | Not Evaluable | Not Evaluable |
| 16 | Head/Neck | Oropharynx | Not Evaluable | Not Evaluable |
| 17 | Sarcoma | Mediastinum | −47 | MR |
| 18 | Bladder | Axilla | −32 | MR |
| 19 | NSCLC | Axilla | −56 | PR |
| 20 | Pancreas | Pancreas | >125 | PD |
| 21 | Melanoma | Pelvis | | |
| 22 | Breast | Thorax | 0 | SD |
| 23 | Rectal | Rectum | −59 | PR |
| 24 | Colorectal | Pelvis | 0 | SD |
| 25 | Lung | Kidney | >−50 | PR |
| 26 | Melanoma | Axilla | +6 | SD |
| 27 | Pancreas | Jejunum | −50 | PR |

Regarding safety, no dose-limiting toxicity was observed over the range of doses of adenoviral vectors tested. No drug-related serious adverse events were experienced by the patients, while minimal adverse events included injection site pain and chills. Significant increases in TNF-α levels in serum above baseline were not observed (1–50 pg/ml) at all time points tested. No virus was detected in cultures taken from blood or urine, and antibody titer against the vector did not increase in seven of eight patients tested.

Regarding efficacy of the treatment protocol, a summary of the tumor responses is provided in the table below, wherein the following abbreviations have the indicated meanings: NSCLC—Non-small cell lung cancer; PR—partial response, more than 50% reduction in volume of the injected lesion; PD—progressive disease, lesion has grown to more than 125% of pre-study value; CR—complete response, complete disappearance of a lesion for at least four weeks from date of documentation; SD—stable disease, tumor is between 75% and 125% of pre-treatment value; MR—reduction to between 50% and 75% of pre-treatment value. PR and CR are routinely regarded as "objective tumor responses."

An objective tumor response was observed in 57% of patients tested, with 28.5% of patients displaying a complete response and 28.5% of patients displaying a partial response. Some tumor shrinkage was achieved in all patients, averaging a decrease in size of 54% in injected lesions. No shrinkage was observed in control lesions. These results prove the effectiveness of the inventive method to treat a wide range of solid tumors, regardless of location in the body.

EXAMPLE 3

This example illustrates use of the inventive method to reduce the size of a tumor associated with soft tissue sarcoma.

Patients with extremity soft tissue sarcomas are selected for treatment using the present inventive method. Patients are injected intratumorally with a pharmaceutical composition comprising one of five dose levels of the TNF-α coding sequence-containing adenoviral vector described in Example 1 ($4 \times 10^9$–$4 \times 10^{12}$ pu in 1½ log increments) over a 5-week therapeutic period. A single dose of pharmaceutical composition is administered via multiple injections to the tumor on day 1 and day 4 of week 1 of the therapeutic period, and once weekly for weeks 2–5. For each dose, the multiple injections are administered to the tumor in parallel lines. Concomitant radiation therapy is initiated in week 1 and administered for five consecutive days, and not administered for two days, for each week of the therapeutic period, achieving a total dose of 30–70 Gy.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law.

Moreover, any combination of the above-described elements in all possible variations thereof is encompassed by the invention unless otherwise indicated herein or otherwise clearly contradicted by context.

What is claimed is:

1. A method for treating a tumor in a human comprising:
   (a) directly administering to the tumor in the human a dose of a pharmaceutical composition comprising (i) a pharmaceutically acceptable carrier and (ii) an adenoviral vector comprising a nucleic acid sequence encoding TNF-α operably linked to an EGR-1 promoter, wherein the dose comprises about $1 \times 10^7$ to about $4 \times 10^{12}$ particle units (pu) of adenoviral vector, at least once a week in a therapeutic period comprising five to ten weeks, and
   (b) administering a dose of ionizing radiation to the tumor over the duration of the therapeutic period, whereby the tumor in the human is treated.

2. The method of claim 1, wherein the size of the tumor is reduced.

3. The method of claim 2, wherein the adenoviral vector is replication-deficient.

4. The method of claim 1, wherein the dose of ionizing radiation comprises about 20 Grays (Gy) to about 70 Gy administered over the duration of the therapeutic period.

5. The method of claim 1, wherein the tumor is a solid tumor.

6. The method of claim 5, wherein the tumor is located in the breast, pancreas, colon, rectum, head, neck, esophagus, or lung.

7. The method of claim 5, wherein the tumor is located in the bladder, thyroid, mandible, skin, or kidney.

8. The method of claim 5, wherein the therapeutic period comprises up to six weeks, and the method comprises administering two doses of pharmaceutical composition in weeks 1–2 and one dose of pharmaceutical composition in each subsequent week of the therapeutic period.

9. The method of claim 5, wherein a dose of the pharmaceutical composition is administered to the tumor via 2–5 injections.

10. The method of claim 1, wherein the tumor is soft tissue sarcoma.

11. The method of claim 10, wherein the therapeutic period comprises five weeks, and the method comprises administering two doses of pharmaceutical composition in week 1 and one dose of pharmaceutical composition in each subsequent week of the therapeutic period.

12. The method of claim 10, wherein a dose of the pharmaceutical composition is administered to the tumor via 3–8 injections.

13. The method of claim 4, wherein the dose of ionizing radiation comprises about 40 Gy to about 60 Gy administered over the duration of the therapeutic period.

14. The method of claim 13, wherein the dose of ionizing radiation comprises about 50 Gy administered over the duration of the therapeutic period.

15. The method of claim 1, wherein the dose of ionizing radiation is administered for five consecutive days in each week of weeks 1–5 of the therapeutic period and not administered for two days in each week of weeks 1–5 of the therapeutic period.

16. The method of claim 1, wherein the method is performed before, during, or after chemotherapy or surgery.

* * * * *

Adverse Decision in Interference

Patent No. 7,214,368, Henrik S. Rasmussen and Karen W. Chu, THERAPEUTIC REGIMEN FOR TREATING CANCER COMPRISING THE ADMINISTRATION OF ADENOVIRAL VECTORS COMPRISING A TNF-A TRANSGENE, Interference No. 105,669, final judgment adverse to the patentees rendered January 26, 2009, as to claims 1-16.

(*Official Gazette,* September 1, 2009)